(12) United States Patent
Lapotko et al.

(10) Patent No.: US 12,201,702 B1
(45) Date of Patent: *Jan. 21, 2025

(54) DIAGNOSIS, REMOVAL, OR MECHANICAL DAMAGING OF TUMOR USING PLASMONIC NANOBUBBLES

(71) Applicant: Masimo Corporation, Irvine, CA (US)

(72) Inventors: Dmitri O. Lapotko, Dana Point, CA (US); Katsiaryna Hleb, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 358 days.

This patent is subject to a terminal disclaimer.

(21) Appl. No.: 16/598,482

(22) Filed: Oct. 10, 2019

Related U.S. Application Data

(63) Continuation of application No. 15/430,321, filed on Feb. 10, 2017, now Pat. No. 10,471,159.

(60) Provisional application No. 62/294,831, filed on Feb. 12, 2016, provisional application No. 62/294,833, filed on Feb. 12, 2016, provisional application No. 62/294,824, filed on Feb. 12, 2016.

(51) Int. Cl.
*A61B 5/00* (2006.01)
*A61K 49/22* (2006.01)

(52) U.S. Cl.
CPC .......... *A61K 49/223* (2013.01); *A61B 5/0095* (2013.01); *A61K 49/221* (2013.01)

(58) Field of Classification Search
CPC ............. A61B 5/0095; A61B 5/4836; A61K 47/6845; A61K 47/6929; A61K 49/22; A61K 49/221; A61K 49/223
See application file for complete search history.

(56) References Cited

U.S. PATENT DOCUMENTS

| 4,174,504 A | 11/1979 | Chenausky |
| 4,818,710 A | 4/1989 | Sutherland |
| 4,960,128 A | 10/1990 | Gordon et al. |

(Continued)

FOREIGN PATENT DOCUMENTS

| WO | WO 2007/104098 | 9/2007 |
| WO | WO 2013/109722 | 7/2013 |
| WO | WO 2019/224822 | 11/2019 |

OTHER PUBLICATIONS

US 2022/0192529 A1, 06/2022, Al-Ali et al. (withdrawn)

(Continued)

*Primary Examiner* — Michael T Rozanski
(74) *Attorney, Agent, or Firm* — Knobbe, Martens, Olson & Bear, LLP

(57) ABSTRACT

Processes of intraoperative diagnosis and elimination of tumors or micro-tumors or cancer cells or tumor microenvironment (TME) with plasmonic nanobubbles (PNBs) are disclosed. The diagnosis and surgical processes disclosed can improve standard onco-surgery through one or more of the following: real-time intraoperative local detection of MRD in vivo with high cancer sensitivity and specificity; real-time guidance of surgery to precisely eliminate resectable MRD with minimal morbidity by resecting only PNB-positive volume instead of a larger volume; intraoperative selective elimination of unresectable MRD through the mechanical impact of lethal cancer cell-specific PNBs without damaging adjacent normal cells and tissues; and prediction of the surgical outcome through the metrics of PNB signals.

18 Claims, 23 Drawing Sheets

(56) References Cited

U.S. PATENT DOCUMENTS

| | | |
|---|---|---|
| 4,964,408 A | 10/1990 | Hink et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,590,649 A | 1/1997 | Caro et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,890,929 A | 4/1999 | Mills et al. |
| 5,919,134 A | 7/1999 | Diab |
| 5,987,343 A | 11/1999 | Kinast |
| 5,997,343 A | 12/1999 | Mills et al. |
| 6,002,952 A | 12/1999 | Diab et al. |
| 6,010,937 A | 1/2000 | Karam et al. |
| 6,027,452 A | 2/2000 | Flaherty et al. |
| 6,040,578 A | 3/2000 | Malin et al. |
| 6,066,204 A | 5/2000 | Haven |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| 6,184,521 B1 | 2/2001 | Coffin, IV et al. |
| 6,232,609 B1 | 5/2001 | Snyder et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,606,511 B1 | 8/2003 | Ali et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| 6,697,656 B1 | 2/2004 | Al-Ali |
| 6,697,658 B2 | 2/2004 | Al-Ali |
| RE38,476 E | 3/2004 | Diab et al. |
| RE38,492 E | 4/2004 | Diab et al. |
| 6,738,652 B2 | 5/2004 | Mattu et al. |
| 6,760,607 B2 | 7/2004 | Al-Ali |
| 6,788,965 B2 | 9/2004 | Ruchti et al. |
| 6,816,241 B2 | 11/2004 | Grubisic |
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,920,345 B2 | 7/2005 | Al-Ali et al. |
| 6,934,570 B2 | 8/2005 | Kiani et al. |
| 6,943,348 B1 | 9/2005 | Coffin, IV |
| 6,956,649 B2 | 10/2005 | Acosta et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Al-Ali |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,225,006 B2 | 5/2007 | Al-Ali et al. |
| RE39,672 E | 6/2007 | Shehada et al. |
| 7,230,708 B2 | 6/2007 | Lapotko et al. |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |

(56) References Cited

U.S. PATENT DOCUMENTS

| | | |
|---|---|---|
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 7,999,161 B2 | 8/2011 | Oraevsky et al. |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,243,272 B2 | 8/2012 | Adams |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Al-Ali |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,155,497 B1 | 10/2015 | Plumley et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B2 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B2 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |

(56) References Cited

U.S. PATENT DOCUMENTS

| | | |
|---|---|---|
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |

(56) References Cited

U.S. PATENT DOCUMENTS

| | | |
|---|---|---|
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| 12,004,869 B2 | 6/2024 | Kiani et al. |
| 12,014,328 B2 | 6/2024 | Wachman et al. |
| D1,036,293 S | 7/2024 | Al-Ali et al. |
| D1,037,462 S | 7/2024 | Al-Ali et al. |
| 12,029,844 B2 | 7/2024 | Pauley et al. |
| 12,048,534 B2 | 7/2024 | Vo et al. |
| 12,064,217 B2 | 8/2024 | Ahmed et al. |
| 12,066,426 B1 | 8/2024 | Lapotko et al. |
| D1,041,511 S | 9/2024 | Indorf et al. |
| D1,042,596 S | 9/2024 | DeJong et al. |
| D1,042,852 S | 9/2024 | Hwang |
| 12,076,159 B2 | 9/2024 | Belur Nagaraj et al. |
| 12,082,926 B2 | 9/2024 | Sharma et al. |
| D1,044,828 S | 10/2024 | Chandran et al. |
| 12,106,752 B2 | 10/2024 | Campbell et al. |
| 12,114,974 B2 | 10/2024 | Al-Ali et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2006/0241459 A1 | 10/2006 | Tai |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2008/0247425 A1 | 10/2008 | Welford |
| 2009/0000614 A1* | 1/2009 | Carrano ............ A61G 13/12 128/118.1 |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0141997 A1 | 6/2009 | Lee et al. |
| 2009/0247984 A1 | 10/2009 | Lamego et al. |
| 2009/0275844 A1 | 11/2009 | Al-Ali |
| 2009/0304033 A1 | 12/2009 | Ogilvy et al. |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0121163 A1 | 5/2010 | Vestel et al. |
| 2010/0222774 A1 | 9/2010 | Hegg et al. |
| 2010/0234718 A1 | 9/2010 | Sampath et al. |
| 2010/0268042 A1 | 10/2010 | Wang |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0172508 A1 | 7/2011 | Chickering, III et al. |
| 2011/0176127 A1 | 7/2011 | Kanda et al. |
| 2011/0189701 A1 | 8/2011 | Kim |
| 2012/0046593 A1 | 2/2012 | Oraevsky et al. |
| 2012/0069860 A1 | 3/2012 | Inbar |
| 2012/0123231 A1 | 5/2012 | O'Reilly |
| 2012/0165629 A1 | 6/2012 | Merritt et al. |
| 2012/0165801 A1 | 6/2012 | Bragagna et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0345921 A1 | 12/2013 | Al-Ali et al. |
| 2014/0012224 A1 | 1/2014 | Zhang |
| 2014/0049190 A1 | 2/2014 | Oh |
| 2014/0120167 A1* | 5/2014 | Lapotko ............ A61K 41/0038 424/490 |
| 2014/0163353 A1 | 6/2014 | Razansky et al. |
| 2014/0166076 A1 | 6/2014 | Kiani et al. |
| 2014/0180160 A1 | 6/2014 | Brown et al. |
| 2014/0182385 A1 | 7/2014 | Oh et al. |
| 2014/0187973 A1 | 7/2014 | Brown et al. |
| 2014/0273188 A1 | 9/2014 | Mohan |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0072337 A1 | 3/2015 | Lapotko et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0351841 A1 | 12/2015 | Whiteside et al. |
| 2016/0166185 A1 | 6/2016 | Liepmann et al. |
| 2016/0196388 A1 | 7/2016 | Lamego |
| 2016/0287141 A1 | 10/2016 | Sidlesky |
| 2016/0341747 A1 | 11/2016 | Ewert |
| 2016/0341945 A1 | 11/2016 | Ou et al. |
| 2016/0367173 A1 | 12/2016 | Dalvi et al. |
| 2017/0016827 A1 | 1/2017 | Gervais et al. |
| 2017/0024748 A1 | 1/2017 | Haider |
| 2017/0173632 A1 | 6/2017 | Al-Ali |
| 2017/0251974 A1 | 9/2017 | Shreim et al. |
| 2018/0000351 A1 | 1/2018 | Zharov |
| 2018/0136193 A1 | 5/2018 | Messerschmidt |
| 2018/0242926 A1 | 8/2018 | Muhsin et al. |
| 2018/0247712 A1 | 8/2018 | Muhsin et al. |
| 2018/0326208 A1 | 11/2018 | Ingman et al. |
| 2018/0344228 A1 | 12/2018 | Yelin |
| 2018/0356418 A1 | 12/2018 | Capocasale |
| 2019/0239787 A1 | 8/2019 | Pauley et al. |
| 2019/0320906 A1 | 10/2019 | Olsen |
| 2019/0345478 A1 | 11/2019 | Lapotko et al. |
| 2019/0374713 A1 | 12/2019 | Kiani et al. |
| 2019/0388069 A1 | 12/2019 | Weber et al. |
| 2020/0060869 A1 | 2/2020 | Telfort et al. |
| 2020/0111552 A1 | 4/2020 | Ahmed |
| 2020/0113520 A1 | 4/2020 | Abdul-Hafiz et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |

(56) References Cited

U.S. PATENT DOCUMENTS

| | | |
|---|---|---|
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0260894 A1 | 8/2024 | Olsen |
| 2024/0267698 A1 | 8/2024 | Telfort et al. |
| 2024/0277233 A1 | 8/2024 | Ai-Ali |
| 2024/0277280 A1 | 8/2024 | Al-Ali |
| 2024/0298920 A1 | 9/2024 | Fernkbist et al. |
| 2024/0306985 A1 | 9/2024 | Vo et al. |
| 2024/0324953 A1 | 10/2024 | Telfort |

OTHER PUBLICATIONS

US 2024/0016391 A1, 01/2024, Lapotko et al. (withdrawn)

Anderson et al., "Optically Guided Controlled Release from Liposomes with Tubable Plasmonic Nanobubbles," Journal of Controlled Release, vol. 144, Issue 2, Jun. 1, 2010, in 22 pages.

Brusnichkin et al., "Determination of Various Hemoglobin Species with Thermal-Lens Spectrometry," Moscow University Chemistry Bulletin, vol. 64, Issue 1, Feb. 2009, pp. 45-54.

Conjusteau et al., "Metallic Nanoparticles as Optoacoustic Contrast Agents for Medical Imaging," SPIE Proceedings, vol. 6086, Photons Plus Ultrasound: Imaging and Sensing 2006: The Seventh Conference on Biomedical Thermoacoustics, Optoacoustics, and Acousto-optics, Mar. 6, 2006, in 9 pages.

Danysh et al., "The MUCI Ectodomain: A Novel and Efficient Target for Gold Nanoparticle Clustering and Vapor Nanobubble Generation," Theranostics, 2, No. 8, Ivyspring International Publisher, 2012, pp. 777-787.

Lapotko et al., "Clusterization of Nanoparticles During their Interaction with Living Cells," Nanomedicine, vol. 2, No. 2, Apr. 2007, pp. 241-253.

Lapotko et al., "Elimination of Leukemic Cells from Human Transplants by Laser Nano-Thermolysis," SPIE Proceedings, vol. 6086, Photons Plus Ultrasound: Imaging and Sensing 2006: The Seventh Conference on Biomedical Thermoacoustics, Optoacoustics, and Acousto-optics, Mar. 6, 2006, in 8 pages.

Lapotko et al., "Lantcet: Novel Laser Nanotechnology for Graft Purging," Biology of Blood and Marrow Transplantation, Feb. 2006, in 2 pages.

Lapotko et al., "Laser Activated Nanothermolysis of Leukemia Cells Monitored by Photothermal Microscopy," SPIE Proceedings, vol. 5697, Photons Plus Ultrasound: Imaging and Sensing 2006: The Seventh Conference on Biomedical Thermoacoustics, Optoacoustics, and Acousto-optics, May 5, 2005, pp. 82-89.

Lapotko et al., "Laser Heating Diagnoses and Treats Cancerous Cells," SPIE Newsroom, The International Society for Optical Engineering, 2006, in 3 pages.

Lapotko et al., "Method of Laser Activated Nano-Thermolysis for Elimination of Tumor Cells," Cancer Letters, vol. 239, Issue 1, Jul. 28, 2006, pp. 36-45.

Lapotko, "Monitoring of Apoptosis in Intact Single Cells with Photothermal Microscope," Journal of the International Society for Advancement of Cytometry, vol. 58A, Issue 2, Apr. 2004, pp. 111-119.

Lapotko, "Optical Excitation and Detection of Vapor Bubbles Around Plasmonic Nanoparticles," Optics Express, vol. 17, Issue 4, Feb. 16, 2009, pp. 2538-2556.

Lapotko et al., "Photothermal and Photoacoustic Processes in Laser Activated Nano-Thermolysis of Cells," SPIE Proceedings, vol. 6437, Photons Plus Ultrasound: Imaging and Sensing 2007: The Eighth Conference on Biomedical Thermoacoustics, Optoacoustics, and Acousto-optics, Mar. 2007, in 13 pages.

Lapotko et al., "Photothermal Detection of Laser-Induced Damage in Single Intact Cells," Lasers in Surgery and Medicine, vol. 33, Issue 5, Dec. 2003, pp. 320-329.

Lapotko et al., "Photothermal Image Cytometry of Human Neutrophils," Journal of the International Society for Advancement of Cytometry, vol. 24, Issue 3, Jul. 1, 1996, pp. 198-203.

Lapotko et al., "Photothermal Response of Live Cells Depends Upon Cell Metabolic State," SPIE Proceedings, vol. 4618, Biomedical Optoacoustics III, Jun. 10, 2002, in 8 pages.

Lapotko et al., "Photothermal Time-Resolved Imaging of Living Cells," Lasers in Surgery and Medicine, vol. 31, Issue 1, Jul. 2002, pp. 53-63.

(56) References Cited

OTHER PUBLICATIONS

Lapotko et al., "Photothermolysis by Laser-Induced Microbubbles Generated Around Gold Nanorod Clusters Selectively Formed in Leukemia Cells," SPIE Proceedings, vol. 6856, Photons Plus Ultrasound: Imaging and Sensing 2008: The Ninth Conference on Biomedical Thermoacoustics, Optoacoustics, and Acousto-optics, Feb. 28, 2008, in 10 pages.

Lapotko, "Plasmonic Nanobubbles as Tunable Cellular Probes for Cancer Theranostics," Cancers, vol. 3, No. 1, 2011 pp. 802-840.

Lapotko, "Plasmonic Nanoparticle-Generated Photothermal Bubbles and their Biomedical Applications," Nanomedicine, vol. 4, No. 7, Oct. 2009, pp. 813-845.

Lapotko, "Nanophotonics and Theranostics: Will Light do the Magic?" Theranostics 2013, vol. 3, Issue 3, pp. 138-140.

Lapotko et al., "Nonstationary Heating and Phase Transitions in a Live Cell in Absorption of Laser Radiation," Heat Transfer Research, vol. 38, Issue 8, Jan. 2007, pp. 695-708.

Lapotko et al., "Selective Laser Nano-Thermolysis of Human Leukemia Cells with Microbubbles Generated Around Clusters of Gold Nanoparticles," Lasers in Surgery and Medicine, vol. 38, Issue 6, Jul. 2006, pp. 631-642.

Lapotko, "Therapy with Gold Nanoparticles and Lasers: What Really Kills the Cells?" Nanomedicine, vol. 4, No. 3, Apr. 2009, pp. 253-256.

Lukianova-Hleb et al., "All-in-one Processing of Heterogeneous Human Cell Grafts for Gene and Cell Therapy," Molecular Therapy— Methods & Clinical Development , vol. 3, Article 16012, 2016, in 8 pages.

Lukianova-Hleb et al., "Cell-Specific Multifunctional Processing of Heterogeneous Cell Systems in a Single Laser Pulse Treatment," ACS Nano, vol. 6, Issue 12, Dec. 21, 2012, pp. 10973-10981.

Lukianova-Hleb et al., "Cell-Specific Transmembrane Injection of Molecular Cargo with Gold Nanoparticle-Generated Transient Plasmonic Nanobubbles," Biomaterials, vol. 33, Issue 21, Jul. 2012, pp. 5441-5450.

Lukianova-Hleb et al., "Hemozoin-Generated Vapor Nanobubbles for Transdermal Reagent and Needle-Free Detection of Malaria," Proceedings of the National Academy of Sciences of the United States of America, vol. 111, No. 3, Jan. 21, 2014, pp. 900-905.

Lukianova-Hleb et al., "Improved Cellular Specificity of Plasmonic Nanobubbles versus Nanoparticles in Heterogeneous Cell Systems," PLoS One, vol. 7, Issue 4, Apr. 2012, in 10 pages.

Lukianova-Hleb et al., "Intraoperative Diagnostics and Elimination of Residual Micro-Tumours with Plasmonic Nanobubbles," Nature Nanotechnology, 2015, in 31 pages.

Lukianova-Hleb et al., "Influence of Transient Environmental Photothermal Effects on Optical Scattering by Gold Nanoparticles," Nano Letters, vol. 9, Issue 5, May 2009, pp. 2160-2166.

Lukianova-Hleb et al., "Laser Pulse Duration is Critical for the Generation of Plasmonic Nanobubbles," Langmuir, vol. 30, Issue 25, 2014, pp. 7425-7434.

Lukianova-Hleb et al., "Malaria Theranostics Using Hemozoin-Generated Vapor Nanobubbles," Theranostics, vol. 4, Issue 7, 2014, pp. 761-769.

Lukianova-Hleb et al., "Multifunctional Cell Processing with Plasmonic Nanobubbles," International Journal of Medical, Health, Biomedical, Bioengineering and Pharmaceutical Engineering, vol. 7, No. 11, 2013, pp. 677-681.

Lukianova-Hleb et al., "Plasmonic Nanobubbles Enhance Efficacy and Selectivity of Chemotherapy Against Drug-Resistant Cancer Cells," Advanced Materials, vol. 24, Issue 28, Jul. 24, 2012, pp. 3831-3837.

Lukianova-Hleb et al., "Plasmonic Nanobubbles for Intracellular Targeting and Gene Therapy," NTSI-Nanotech 2011, vol. 3, pp. 291-294.

Lukianova-Hleb et al., "Plasmonic Nanobubbles as Transient Vapor Nanobubbles Generated Around Plasmonic Nanoparticles," ACS Nano, vol. 4, Issue 4, Apr. 27, 2010, pp. 2109-2123.

Lukianova-Hleb et al., "Plasmonic Nanobubble-Enhanced Endosomal Escape Processes for Selective and Guided Intracellular Delivery of Chemotherapy to Drug-Resistant Cancer Cells," Biomaterials, vol. 33, Issue 6, Feb. 2012, pp. 1821-1826.

Lukianova-Hleb et al., "Plasmonic Nanobubbles Rapidly Detect and Destroy Drug-Resistant Tumors," Theranostics, vol. 2, No. 10, 2012, pp. 976-787.

Lukianova-Hleb et al., "Plasmonic Nanobubbles as Tunable Theranostic Agents," NSTI-Nanotech 2011, vol. 3, pp. 367-370.

Lukianova-Hleb et al., "Plasmonic Nanobubbles: Tunable and Transient Probes for Cancer Diagnosis, Therapy and Theranostics," NSTI-Nanotech 2010, vol. 3, 2010 in 5 pages.

Lukianova-Hleb et al., "Rainbow Plasmonic Nanobubbles: Synergistic Activation of Gold Nanoparticle Clusters," Journal of Nanomedicine & Nanotechnology, vol. 2, Issue 104, Jan. 1, 2011, in 21 pages.

Lukianova-Hleb et al., "Safety and Efficacy of Quadrapeutics Versus Chemoradiation in Head and Neck Carcinoma Xenograft Model," American Journal of Cancer Research, vol. 5, Issue 12, 2015, pp. 3534-3547.

Lukianova-Hleb et al., "Selective Gene Transfection of Individual Cells In Vitro with Plasmonic Nanobubbles," Journal of Controlled Release, vol. 152, Issue 2, Jun. 10, 2011, pp. 286-293.

Lukianova-Hleb et al., "Selective and Self-Guided Micro-Ablation of Tissue with Plasmonic Nanobubbles," Journal of Surgical Research, vol. 166, Issue 1, Mar. 2011, pp. e3-e13.

Lukianova-Hleb et al., "Short Laser Pulse-Induced Irreversible Photothermal Effects in Red Blood Cells," Lasers in Surgery and Medicine, vol. 43, Issue 3, Mar. 2011, pp. 249-260.

Lukianova-Hleb et al., "Transdermal Diagnosis of Malaria Using Vapor Nanobubbles," Emerging Infectious Diseases, vol. 21, No. 7, Jul. 2015, pp. 1122-1127.

Lukianova-Hleb et al., "Transient Enhancement and Spectral Narrowing of the Photothermal Effect of Plasmonic Nanoparticles Under Pulsed Excitation," Advanced Materials, Voume 25, Issue 5, Feb. 6, 2013, pp. 772-776.

Lukianova-Hleb et al., "Transient Photothermal Spectra of Plasmonic Nanobubbles," Langmuir, vol. 28, Issue 10, Feb. 2012, pp. 4858-4866.

Lukianova-Hleb et al., "Tunable Plasmonic Nanobubbles for Cell Theranostics," Nanotechnology, vol. 21, No. 8, Feb. 26, 2010, in 19 pages.

Lukianova-Hleb et al., "Tunable Plasmonic Nanoprobes for Theranostics of Prostate Cancer," Theranostics, vol. 1, 2011, pp. 3-17.

Potkin et al., "The Influence of Heterocyclic Compound-Pamam Dendrimer Complexes on Evoked Electrical Responses in Slices of Hypoxic Brain Tissue," Cellular & Molecular Biology Letters, vol. 19, 2014, pp. 243-248.

Vasiliev et al., "Bubble Generation in Micro-Volumes of 'nonofluids'," International Journal of Heat and Mass Transfer, vol. 52, Issues 5-6, Feb. 2009, pp. 1534-1539.

Lukianova-Hleb et al., "Experimental Techniques for Imaging and Measuring Transient Vapor Nanobubbles," Applied Physics Letters, vol. 101, Dec. 2012, pp. 264102-1-264102-5.

Lukianova-Hleb et al., "Plasmonic Nanobubbles for Cell Theranostic," Proceedings of SPIE, 2012, vol. 8234, pp. 82341F-1-82341F-10.

Lukianova-Hleb et al., "Generation and Detection of Plasmonic Nanobubbles in Zebrafish," Nanotechnology, vol. 21, No. 22, Jun. 4, 2010, in 22 pages.

Choi et al., A High Throughput Microelectroporation Device to Introduce a Chimeric Antigen Receptor to Redirect the Specificity of Human T Cells, Biomed Microdevice, 2010, 12, pp. 855-863.

\* cited by examiner

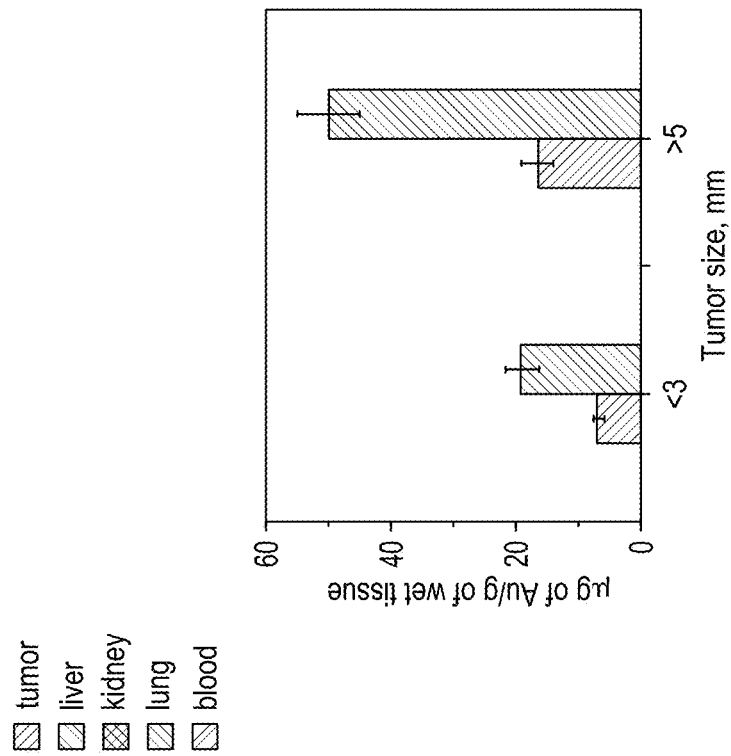
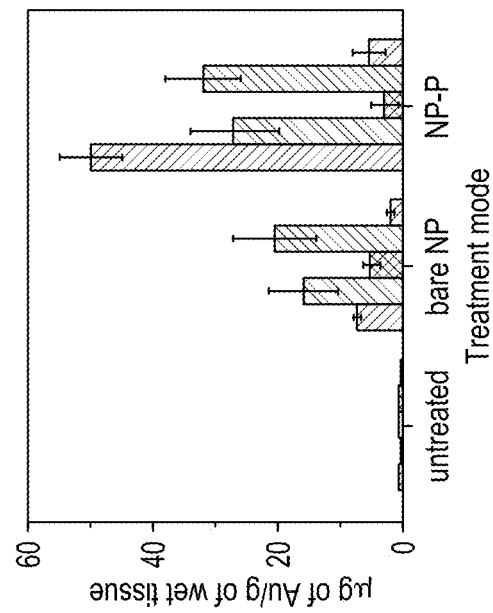
FIG. 10A
FIG. 10B

DIAGNOSIS, REMOVAL, OR MECHANICAL DAMAGING OF TUMOR USING PLASMONIC NANOBUBBLES

INCORPORATION BY REFERENCE TO ANY PRIORITY APPLICATIONS

The present application is a continuation of U.S. patent application Ser. No. 15/430,321, filed Feb. 10, 2017, entitled "DIAGNOSIS, REMOVAL, OR MECHANICAL DAMAGING OF TUMOR USING PLASMONIC NANOBUBBLES," which claims priority benefit under 35 U.S.C. § 119(e) to U.S. Patent Application No. 62/294,833, entitled "INTRAOPERATIVE DIAGNOSIS OF TUMORS AND RESIDUAL MICRO-TUMORS AND TUMOR MICRO-ENVIRONMENT WITH PLASMONIC NANOBUBBLES," filed Feb. 12, 2016, U.S. Patent Application No. 62/294,831, entitled "INTRAOPERATIVE DIAGNOSIS OF TUMORS AND RESIDUAL MICRO-TUMORS AND TUMOR MICRO-ENVIRONMENT WITH PLASMONIC NANOBUBBLES," filed Feb. 12, 2016, and to U.S. Patent Application No. 62/294,824, entitled "INTRAOPERATIVE DIAGNOSIS OF TUMORS AND RESIDUAL MICRO-TUMORS AND TUMOR MICRO-ENVIRONMENT WITH PLASMONIC NANOBUBBLES," filed Feb. 12, 2016; each of the foregoing applications is hereby incorporated by reference herein in its entirety.

BACKGROUND

The present application relates generally to the fields of cancer cell or residual microtumor detection and elimination. More particularly, the present application relates to intraoperative diagnostic and elimination of cancer cells in vivo.

SUMMARY

Despite continuous improvements in onco-surgery, residual micro-tumors (microscopic residual disease—MRD) remain a significant problem. In many aggressive cancers, including head and neck squamous cell carcinoma (HNSCC), brain, lung and breast cancer, and sarcomas, what appears to be a complete tumor resection may leave MRD behind, often as small as tens of cancer cells, that later causes lethal recurrence. Clinical standards such as palpation and radiographic imaging are not sensitive enough to detect MRD. Pathological analysis of surgical margins, the only currently available MRD diagnostics, is slow, often inaccurate and not always available. As a result, surgeons routinely resect large margins of normal tissue to remove potential MRD. Unfortunately, this approach often fails, causes high morbidity and reduces patients' quality of life and eligibility. Post-operative radiation or chemoradiation therapies further increase the morbidity and treatment cost, and reduce patients' quality of life. Further, MRD often becomes highly resistant to radiation or chemotherapy resulting in poor survival. Similar needs of detecting cancer cells exist in in ex vivo tissue grafts and in veterinary medicine.

Today's diagnostic technologies cannot detect MRD in solid tissue in vivo with single cancer cell sensitivity and in real time. "Real Time" as used herein includes a broad ordinary meaning recognizable to one of ordinary skill in the art which includes the providing of output information responsive to the described processing of input data sufficiently quickly to allow a caregiver to affect the environment in which they are operating, using the output information as feedback. In any event, "Real Time" as used herein includes at least electronic processing delay times. As a result, those diagnostic technologies are limited in any reduction in local recurrence and improvement in overall survival for MRD-complicated surgeries. For example, while optical approaches improved cancer detection in vivo including intraoperative fluorescent and optical scattering diagnostics, they detect only relatively large tumors at the surface while MRD can be located deeper in tissue and can be of a microscopic size. Photoacoustic methods detect tumors in depths up to 10-20 mm although with limited sensitivity in solid tissue (>1000 cells), speed and specificity for intraoperative detection of MRD in a surgical bed. Radio-fluorescent methods can detect deeper tumors but are not sensitive enough for MRD detection. Multi-spectral optoacoustic tomography is used intraoperatively, but is not sensitive or fast enough to detect MRD (which can be represented by tens of cancer cells) in vivo in solid tissue in real time, and did not show a good surgical outcome in MRD applications. Furthermore, standard surgery often cannot remove MRD even when identified by frozen section pathology without causing too high morbidity because MRD infiltrates into critical organs.

In addition, a tumor micro-environment ("TME") could still exist after removal of cancer cells. Examples of TME include non-tumor targets that are biologically associated with a tumor, such as tumor blood vasculature and other components that are understood by one of ordinary skill in the art. Blood flow in the vasculature may cause tumor metastases of cancer cells or recurrence of tumor.

The present disclosure provides the ability to intraoperatively detect and precisely eliminate tumor and MRD in vivo in real time in resectable and in unresectable cases, and to intraoperatively detect and precisely eliminate TME, including tumor blood vasculature, either as a stand-alone or an intraoperative adjuvant treatment of residual tumor, to significantly improve the treatment outcome, treatment eligibility and quality of life for cancer patients and would reduce surgical morbidity. The present disclosure also provides the ability to detect cancer cells in tissue grafts and in veterinary medicine.

An objective of various embodiments of the present disclosure is to provide a plasmonic nanobubbles ("PNB"s)-guided in vivo and ex vivo diagnosis of tumors, microtumors, cancer cells, MRD and TME with high speed and cancer specificity in real time during a surgery. In some embodiments, the diagnosis can be applied to resectable tumors, unresectable tumors, or both or any specific target cells. In some embodiments, the diagnosis can be applied to TME. In some embodiments, the diagnosis can be applied to both tumor cells and TME. In accordance various embodiments disclosed herein, a process for noninvasive PNB-guided intraoperative detection of cancer cells in vivo comprises administering to a patient nanoparticles conjugated with cancer-specific antibodies (or other ligands) at a predetermined time prior to a diagnostic procedure; performing the diagnostic procedure comprising directing a first pulsed source of electromagnetic radiation having a predetermined level of energy against a first location on the patient to generate a first group of PNBs around the nanoparticles clustered in the cancer cells; detecting a first pressure pulse emitted by the first group of PNBs with an acoustic detector; transmitting a signal from the first pressure pulse to a signal processing unit to register a first acoustic time-response; and comparing the first acoustic time-response with a PNB-negative time-response to determine whether the first acoustic time-response meets a PNB-positive threshold. In accordance with various embodiments disclosed herein, the nanoparticles are capable of absorption and plasmonic conversion of electromagnetic radiation with wavelength in the near infrared region into the localized heat in and around plasmonic nanoparticle. In accordance with various embodiments disclosed herein, the electromagnetic radiation comprises a short laser pulse.

In some embodiments of the present disclosure, a system configured to noninvasively determine in real time a presence, a location and a depth of unwanted cells including cancer cells or microtumors or tumor-specific vasculature in tissue using PNBs during an intraoperative diagnostic procedure is provided. The system can include a plurality of bioconjugated nanoparticles configured to be administered to a patient at a predetermined time prior to a diagnostic procedure, a source of electromagnetic radiation configured to provide a plurality of pulses at a plurality of energy levels to tissue at a measurement site, an acoustic detector configured to output signals responsive to a plurality of pressure pulses emitted by PNBs from at least some of the bioconjugated nanoparticles in the cancer cells, and a signal processor configured to receive said signals or one or more pre-processed signals responsive to said signals and configured to process said signals or said one or more pre-processed signals. The bioconjugated nanoparticles can comprise a plurality of nanoparticles and a plurality of cancer-specific or tumor-associated vasculature-specific ligands configured to attach to and cluster in said unwanted cells. The processing can include determining a first acoustic time-response from said signals or said pre-processed signals corresponding to pulse of said source at a first energy level, comparing said first acoustic time-response with a PNB-negative time-response, when said comparison is negative, outputting notification indicia usable by a caregiver to determine the presence of said unwanted cells at a first depth in said tissue at said measurement site, and when said presence of said cancer cells is determined, additionally determining another acoustic time-response from said signals or said pre-processed signals corresponding to pulses of said source at an increased energy level. The increased energy level can be configured to cause said pulses of said source to reach tissue at an increased depth. The processing additionally can include comparing said another acoustic time-response with said PNB-negative time-response, when said comparison is negative, additionally outputting notification indicia usable by said caregiver to determine the presence of said unwanted cells at the increased depth in said tissue at said measurement site, and repeating said additionally determining, comparing and outputting until said additional comparing is positive.

In some embodiments of the present disclosure, a noninvasive real-time process to determine a presence, a location and a depth of cancer in tissue using plasmonic nanobubbles ("PNBs") is disclosed. The process can include administering bioconjugated nanoparticles to a patient, the bioconjugated nanoparticles comprising a plurality of nanoparticles and a plurality of bonded cancer-specific or tumor-associated vasculature-specific ligands; emitting with a laser source a laser pulse at an energy to tissue at a measurement site of said patient to generate a group of PNBs; detecting with a detector one or more pressure pulses from said group of PNBs; transmitting to a signal processor signals responsive to said detected sounds; processing with said signal processor said signal, said processing including determining a time-response; comparing the time-response to a threshold; when said time-response is less than said threshold, outputting indicia to a monitor reviewed by a caregiver, said indicia usable to conclude cancer cells exist in said tissue at a depth; and when said time-response is less than said threshold, increasing said energy of said laser pulse and repeating said detecting, transmitting, and said processing to determine whether said cancer cells exist in said tissue at an increase of said depth.

In some embodiments of the present disclosure, a system usable in the resection of cancer cells or microtumors that improves therapeutic efficacy and reduced morbidity of standard surgery is disclosed. The system can include a source of electromagnetic radiation, a PNB probe configured to irradiate tissue of a patient including bioconjugated nanoparticles to produce PNBs in said tissue, a detector configured to output a signal responsive to pressure pulses of said PNBs, and a signal processor configured to process information responsive to said signals to generate an output usable by a clinician to determine whether to resect portions of said tissue defined by a footprint of said PNB probe. Said source can be configured to, when needed, provide said PNB probe increasing levels of radiation pulses to reach increasing depths of said tissue. The system can further comprise a surgical apparatus configured to position or house said PNB probe. Said surgical apparatus can comprise a robotic surgical arm. Said surgical apparatus can comprise a laparoscopic tool. Said surgical apparatus can comprise an endoscope.

In some embodiments of the present disclosure, a process that guides a surgeon in the resection of cancer cells or microtumors is provided. The process can include irradiating with a PNB probe having a source of electromagnetic radiation tissue of a patient including bioconjugated nanoparticles to produce plasmonic nanobubbles ("PNB") in said tissue, outputting from a detector a signal responsive to pressure pulses of said PNBs, processing with a digital signal processor information responsive to said signals; and generating an output usable by a surgeon to determine whether to resect portions of said tissue defined by a footprint of said PNB probe. Said source can be configured to, when needed, provide said PNB probe increasing levels of radiation pulses to reach increasing depths of said tissue. Said irradiating, outputting, processing, and generating can repeat with each resection of said portion of said tissue to monitor outcome of a previous resection. Said generating an output can comprise generating said output directing said surgeon to relocate said PNB probe to a different portion of said tissue. Said generating an output can comprise generating said output directing said surgeon to resect more of said portion even when said processing does not indicate detection of said PNBs. Said generating an output can comprise generating said output directing said surgeon to probe deeper into said portions of said tissue. Probing deeper can comprise said irradiating, outputting, processing, and generating using an increased energy of said radiation. Said processing using said increased energy can comprise comparing a peak-to-peak amplitude of said signals to a cancer-free signal. Said processing using said increased energy can comprise determining a time delay between an activation of said source and a detection of said pressure pulses and comparing said delay with known delay information. Said irradiating using said increased energy can comprise pulsing said source at a laser pulse fluence of between 10 and 120 mJ/cm$^2$. Said pulsing said source at said laser pulse fluence can comprise pulsing said source at about 60 mJ/cm$^2$. Said irradiating can comprise pulsing said source for a duration not exceeding about 100 ps. Said irradiating can comprise pulsing said source for a duration of about 30 ps. Said energy levels can exceed a PNB generation threshold.

In some embodiments of the present disclosure, a system for eliminating non-operable cancer cells or tumor-specific vasculature to improve the outcome in unresectable cases with a PNB "nano-surgery" mode is disclosed.

In some embodiments of the present disclosure, a system for eliminating non-operable unwanted cells including one or more of cancer cells or tumor-associated vasculature is disclosed. The system can comprise a source of electromagnetic radiation, a PNB probe configured to irradiate tissue of a patient including bioconjugated nanoparticles to produce plasmonic nanobubbles ("PNBs") in said tissue, said source configured to provide said PNB probe increasing levels of radiation pulses including increasing detection-level radiation and increasing destruction-level radiation, a detector configured to output a signal responsive to pressure pulses of said PNBs, and a signal processor configured to process information responsive to said signals and to increase the level of the laser pulse energy or fluence from detection-level radiation to destruction-level radiation to selectively destroy said unwanted cells by a mechanical impact generated from an explosive effect of the PNBs. The signal processor can be further configured to increase the detection-level radiation, when needed, and correspondingly to increase the destruction-level radiation. The signal processor can be further configured to monitor destruction of said cancer cells through a peak-to-peak amplitude of an output of said signal processor. The signal processor can be further configured to cause said increase until said pressure pulses of said PNBs indicate no further cancer cells in said tissue. The detection-level radiation can exceed a PNB generation threshold. The detection-level radiation can be between 10 and 120 mJ/cm$^2$ for an about 25 ps pulse. The detection-level radiation can be 60 mJ/cm$^2$ for an about 25 ps pulse. Said destruction-level radiation is sufficient to generate PNBs with a size exceeding a cancer cell damage threshold. At least some PNBs of the system can be of a size exceeding a cancer cell damage threshold and some PNBs can be of a size below a cancer damage threshold after said destruction-level radiation. The destruction-level radiation can be between 40 and 400 mJ/cm$^2$ for an about 25 ps pulse. The destruction-level radiation can be 120 mJ/cm$^2$ for an about 25 ps pulse. The source can be configured to provide said radiation pulses with a duration not exceeding about 100 ps. The source can be configured to provide said radiation pulses with a duration of about 30 ps. The signal processor can be further configured to generate an output directing a surgeon to relocate said PNB probe to a different portion of said tissue. The signal processor can be further configured to generate an output directing a surgeon to increase the level of the laser pulse energy or fluence from said detection-level radiation to said destruction-level radiation even when said output does not indicate detection of said PNBs. The signal processor can be further configured to generate an output directing a surgeon to probe deeper into said portions of said tissue. Probing deeper can comprise increasing said detection-level radiation. The bioconjugated nanoparticles can be configured to produce PNBs in cancer cells. The bioconjugated nanoparticles can be configured to produce PNBs in tumor-associated vasculature. The bioconjugated nanoparticles can be configured to produce PNBs in one or more of cancer cells or tumor-associated vasculature, wherein a first group of bioconjugated nanoparticles can be configured to attach to and cluster in said cancer cells and a second group of bioconjugated nanoparticles can be configured to attach to and cluster in said tumor-associated vasculature. The first and second groups of bioconjugated nanoparticles can be the same. The first and second groups of bioconjugated nanoparticles can be different.

In some embodiments, a cancer detection system configured to noninvasively determine a presence of unwanted cancerous material in tissue using plasmonic nanobubbles ("PNBs") is disclosed, said cancer detection system returning post-electronic processing results to an operator at least at each measurement site during a cancer detection procedure. Said cancer detection system can comprise a plurality of bioconjugated nanoparticles configured to be administered to a patient at a predetermined time prior to said cancer detection procedure, the bioconjugated nanoparticles comprising a plurality of nanoparticles and a plurality of cancerous material-specific ligands configured to attach to and cluster in said unwanted cancerous material; a source of electromagnetic radiation configured to provide a plurality of radiation pulses at a plurality of energy levels to said tissue at said measurement site; and an acoustic detector configured to output signals responsive to a plurality of pressure pulses emitted by PNBs from at least some of the bioconjugated nanoparticles when said tissue includes said unwanted cancerous material; and one or more signal processors operably communicating with said acoustic detector and configured to receive said output signals or one or more pre-processed signals responsive to said signals, configured to electronically process said signals or said one or more pre-processed signals, and configured to notify said operator with a result of said processing at each measurement site, said processing including determining a first acoustic time-response responsive to said signals or said pre-processed signals corresponding to one or more of said pulses of said source at a first energy level; comparing said first acoustic time-response with a PNB-negative time-response to determine a detection of the PNBs; and when a sufficient amount of said presence is determined, returning a positive result for said presence of said unwanted cancerous material. The system can be configured to noninvasively determine a depth of unwanted cancerous material, wherein said one or more signal processors electronically process said signals or said one or more pre-processed signals. The processing can further include determining another acoustic time-response responsive to said signals or said pre-processed signals corresponding to one or more of said pulses of said source at an increased energy level, the increased energy level configured to cause said pulses of said source to reach tissue at an increased depth; comparing said another acoustic time-response with said PNB-negative time-response; when said comparison is negative, additionally returning a positive result for said presence of said unwanted cancerous material at the increased depth in said tissue at said measurement site; and repeating said determining using said increasing energy levels, comparing and returning until said additional comparing is positive and said one or more processors return a negative result for said unwanted cancerous material at the increased depth. Said cancerous material can include cancer cells, cancerous microtumors, or cancerous tumor associated vasculature. Said source can provide said plurality of said pulses, at least some of said pulses provided at wavelengths between about 600 and about 1,500 nm. Said source can provide said plurality of said pulses, at least some of said pulses provided at a wavelength of about 782 nm. Said source can provide said plurality of said pulses, at least some of said pulses having a duration not exceeding about 100 ps. Said duration can be about 30 ps. The system can further comprise a medical apparatus configured to position or house said source. Said medical apparatus can comprise a robotic arm. Said medical apparatus can comprise a laparoscopic tool. Said medical apparatus can comprise an endoscope. The cancerous material-specific ligands can comprise an antibody. The antibody can comprise different antibodies.

In some embodiments, a noninvasive process to determine cancer in tissue using plasmonic nanobubbles ("PNBs") is disclosed. Said process can comprise administering bioconjugated nanoparticles to a patient, the bioconjugated nanoparticles comprising a plurality of nanoparticles and a plurality of bonded cancer-specific or tumor-associated vasculature-specific ligands; emitting from a laser source a laser pulse at an energy to tissue at a measurement site of said patient; detecting with a detector one or more pressure pulses from a group of PNBs, if any, responsive to said laser pulse; electronically processing with one or more signal processors, one or more signals responsive to said detecting, said processing can include electronically determining a time-response; electronically comparing the time-response to a threshold; and when said time-response is greater than said threshold, outputting indicia to a monitor, said indicia usable to conclude one or more of cancer cells or tumor-specific vasculature exist in said tissue. When said time-response is greater than said threshold, the process can further comprise increasing said energy of said laser pulse and repeating said detecting, transmitting, and said processing to determine whether said cancer cells or tumor-specific vasculature exist in said tissue at an increase of said depth. Said repeating can terminate when said time-response is less than said threshold. When said time-response is greater than said threshold, the process can further comprise generating an output usable by a surgeon to determine whether to resect portions of said tissue defined by a footprint of said PNB probe. Said emitting, outputting, processing, and generating can repeat with each resection of said portion of said tissue.

BRIEF DESCRIPTION OF THE DRAWINGS

The drawings and following associated descriptions are provided to illustrate embodiments of the present disclosure and do not limit the scope of the claims. Corresponding numerals indicate corresponding parts.

FIG. 10A illustrates an exemplary influence of tumor-specific antibodies on biodistribution of gold nanoparticles.

FIG. 10B illustrates an exemplary influence of tumor size on accumulation of gold nanoparticles in a tumor.

DETAILED DESCRIPTION

Aspects of the disclosure are provided with respect to the figures and various embodiments. One of skill in the art will appreciate, however, that other embodiments and configurations of the devices and methods disclosed herein will still fall within the scope of this disclosure even if not described in the same detail as some other embodiments. Aspects of various embodiments discussed do not limit scope of the disclosure herein, which is instead defined by the claims following this description.

The term "energy" in this disclosure includes its broad ordinary meaning understood by an artisan, and also is shorthand for "fluence," which has its broad ordinary meaning understood by an artisan to include energy per area squared.

Combining the intraoperative detection of single cancer cells in a surgical bed, real-time elimination of MRD and prediction of the surgical outcome is the ultimate desire for surgical oncologists. Embodiments of this disclosure can achieve this and other multi-functionality through a PNB technology with high cancer cell sensitivity, specificity, speed and translational potential.

Figure 1A:
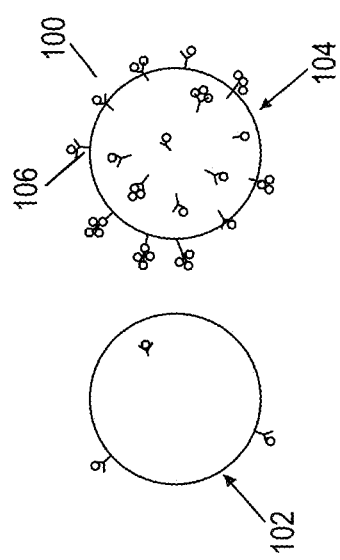
FIGS. 1A-1C illustrate known principles of plasmonic nanobubble ("PNB") formation in isolated cells.
Figure 1B:
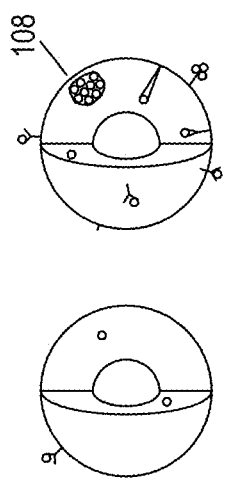
Figure 1C:
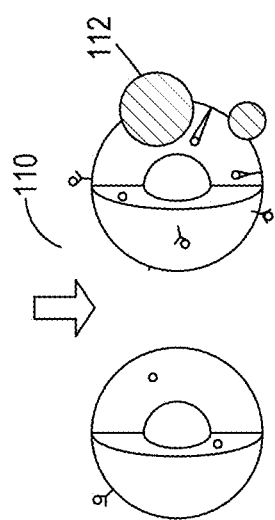

The application of plasmonic nanobubbles (PNBs) technology to target cancer cells ex vivo has been described, for example, in U.S. Pat. No. 7,999,161 to Oraevsky et al., the contents of which are incorporated herein by reference in their entirety. FIGS. 1A-1C illustrate known principles of interactions of bioconjugated nanoparticles 100 with an isolated normal cell 102 and an isolated tumor cell 104. Nanoparticles 100 which are capable of absorption and plasmonic conversion of energy from a source of electromagnetic radiation are covalently conjugated with cancer-specific monoclonal antibodies in order to target receptors 106 found on a surface of the tumor cell, for example, an epidermal growth factor receptor, but not found on a surface of the normal cell. As a result, when introducing the bioconjugated nanoparticles 100 to the tumor cell 104, the nanoparticles 100 are adsorbed onto on the surface of the tumor cell via the receptors and eventually form nanoparticle clusters 108 inside the tumor cell. In contrast, the nanoparticles 100 are seldom taken up by the normal cell 102 due to lack to cancer-specific receptors on its surface, and no cluster is formed in the cytoplasm of the normal cell. Applying a pulsed source of electromagnetic radiation, such as a laser pulse 110, to the cancer cell 104 containing the nanoparticle clusters 108 can cause a nanobubble 112 to be formed from the rapid evaporation of liquid around the overheated cluster 108 due to the absorption and plasmonic conversion of the laser pulse energy, whereas the same laser pulse energy is not sufficient to excite the few isolated nanoparticles 100 that are occasionally taken up by the normal cell 102. The rapid expansion and collapse of the vapor nanobubble 112 can identify the existence of tumor cell 104, can guide resection thereof, and can cause mechanical impact on and can destroy the tumor cell 104.

Cancer Cell Detection and Elimination

Figure 2:
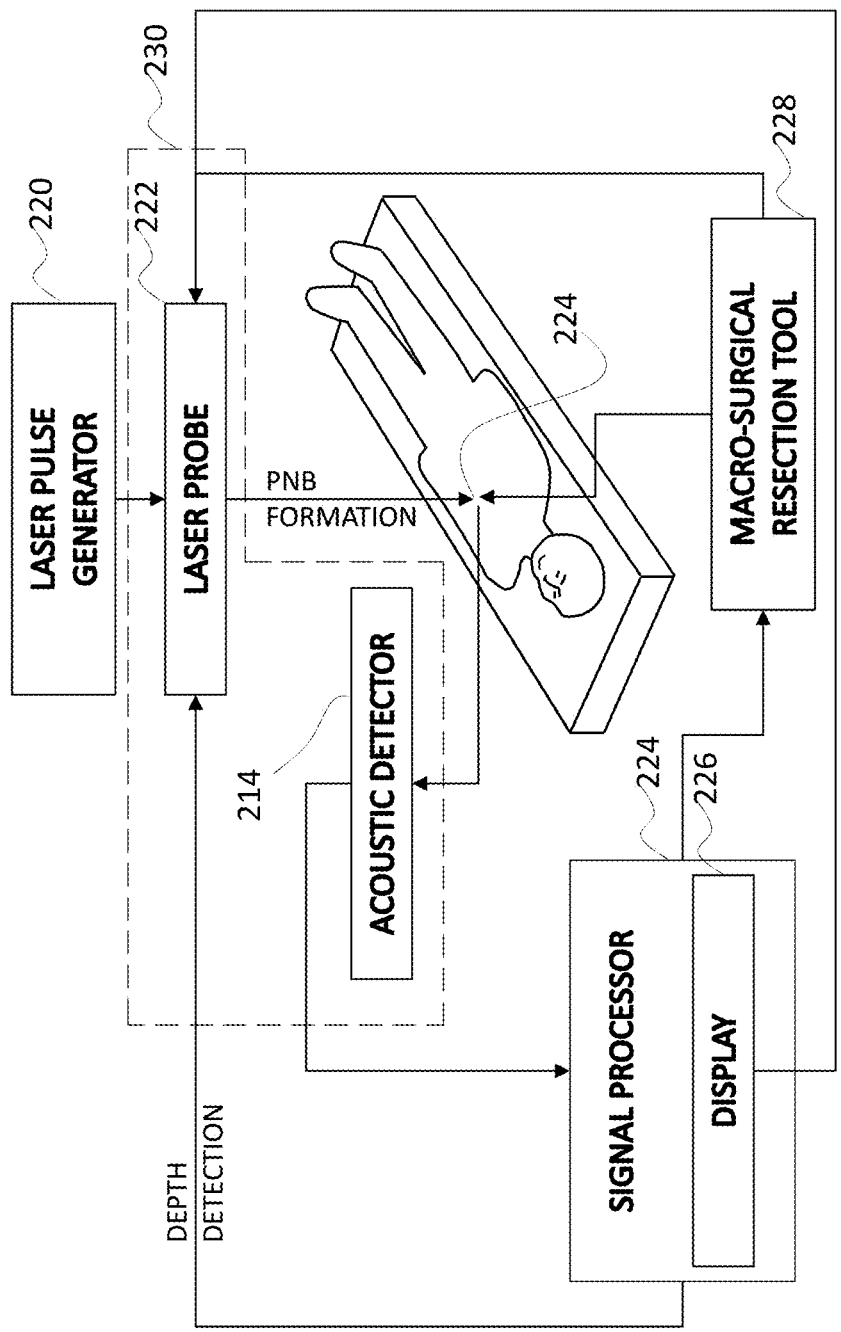
FIG. 2 illustrates a block drawing of a cancer cells detection and elimination system in accordance with an embodiment of the disclosure.

FIG. 2 illustrates a schematic drawing of a cancer cells detection and elimination system in accordance with an embodiment of the disclosure. The system will be described below in detail in connection with the descriptions of FIGS. 2A-2D and FIGS. 3-6.

Figure 2A:
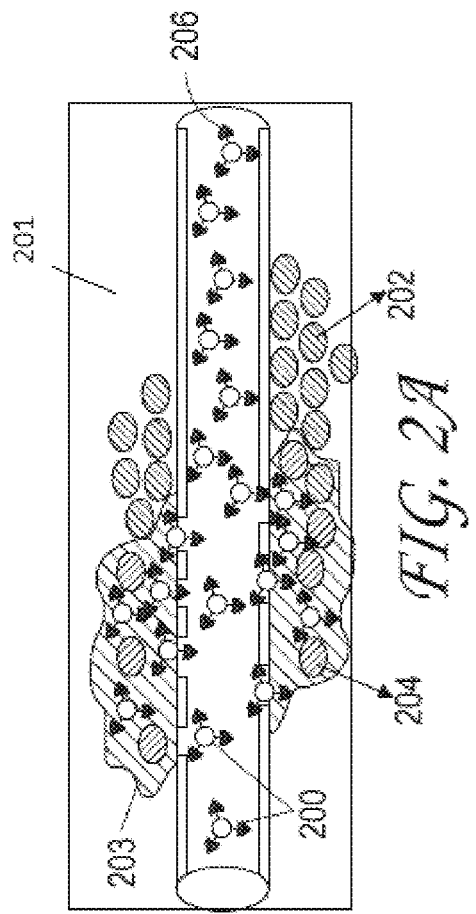
FIG. 2A-2D illustrate the delivery and clustering of gold nanoparticles, generation and detection of PNB in cancer cells in vivo.
Figure 8B:
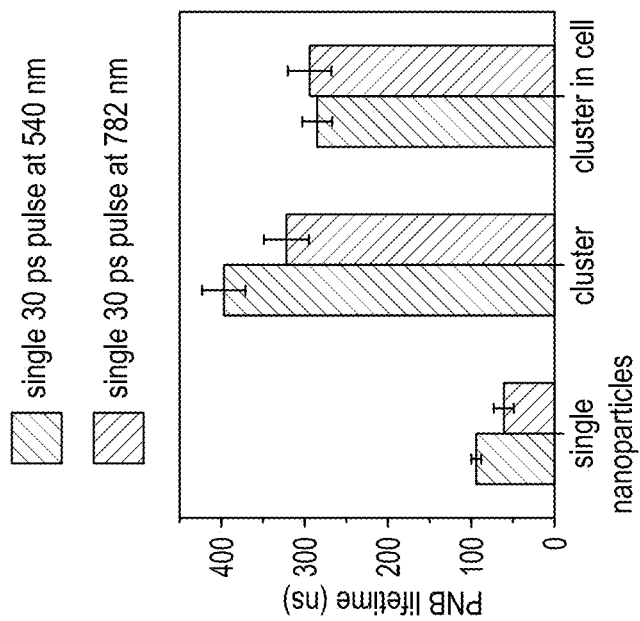
FIG. 8B illustrates an exemplary comparison of PNB lifetime of the gold nanoparticles in FIG. 8A under non-stationary optical excitation.
Figure 8A:
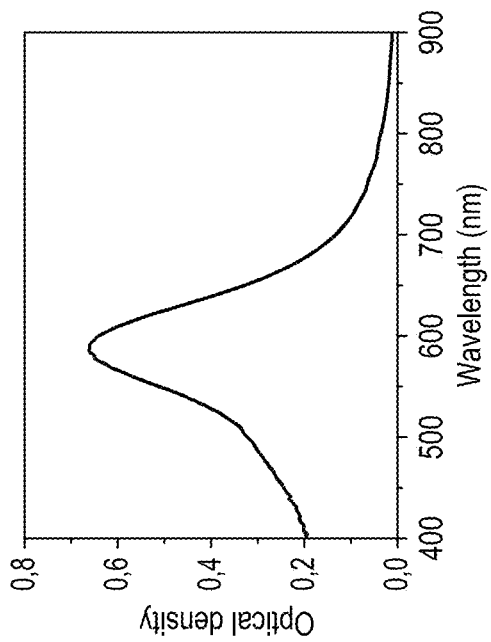
FIG. 8A illustrates an exemplary stationary optical excitation spectrum showing photothermal efficacy of gold spherical nanoparticles conjugated to Panitumumab.

FIGS. 2A-2D illustrate detection of cancer cells in vivo. FIG. 2A illustrates administration of nanoparticle conjugates 200 into the patient's body including normal tissue 201 having normal cells 202, and tumor tissue 203 having cancer cells 204. As electromagnetic radiation in the visible region can have difficulty penetrating solid tissue, nanoparticles that demonstrate high optical absorbance in the near-infrared (NIR) range, such as a laser pulse 210, can be used. Nanoparticles that have low toxicity to patients as well as the ability to be excited by an NIR pulse are suitable candidates for nanobubble generation. At least partially metallic nanoparticles, such as gold nanoparticles, can have desirable biosafety (see Example 3 below), but have a peak of optical absorbance in the visible light range if under a stationary source of electromagnetic radiation (FIG. 8A). Nevertheless, as shown in FIG. 8B and explained in greater detail below in Example 2, off-resonant excitation of such nanoparticles can be achieved by using non-stationary pulsed laser energy with duration in the range of picoseconds. The duration of the pulse can be between about 1 ps to 1000 ps. For example, it would be advantageous to keep the duration of the pulse below 100 ps, although an artisan will recognize from the disclosure herein other durations. Using gold as an example (FIGS. 2A-2D), gold nanoparticles used for making gold colloid conjugates 200 can be between 10 to 300 nm in the largest dimension and can be of any shape. In some embodiments, the gold nanoparticles can be 60 nm spheres. To form clusters 208 in vivo, gold nanoparticles 200 conjugated with any cancer-specific antibodies 206 or other ligands to recognize cancer cells, such as Panitumumab, can be systemically administered. In some embodiments, the gold conjugate can be administered intravenously at a dose that results in negligible short-term and long-term toxicity. The gold conjugate can be administered in the amount of between about 0.1 mg/kg to about 20 mg/kg body weight, or between about 1 mg/kg to about 40 mg/kg body weight. In some embodiments, the gold conjugate can be administered in the amount of about 4 mg/kg body weight. The gold conjugate can be administered at between about 1 hour to about 36 hours prior to a diagnostic procedure or an onco-surgery. In some embodiments, the gold conjugates can be administered at least about 24 hours prior to a diagnostic procedure or an onco-surgery. Alternatively, the bioconjugated nanoparticles can be locally injected prior to apply a laser pulse. Example 2 below provides in greater detail several mechanisms for forming in vivo intracellular clusters of gold colloids as PNB sources. As described above and shown in FIGS. 2B and 2C, the gold conjugates 200 are attached onto a surface of the cancer cells, but are seldom attached onto a surface of a normal cell.

Figure 2B:
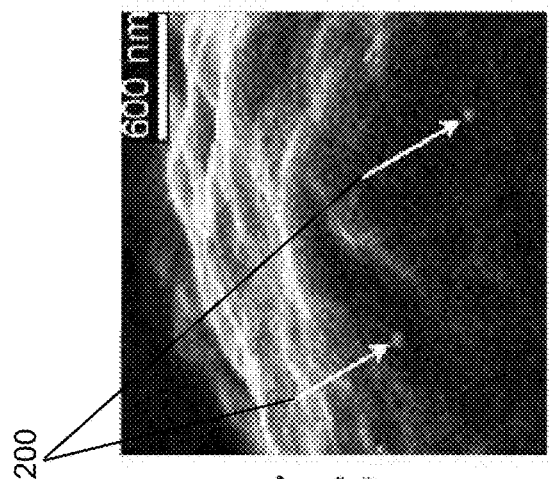
Figure 2B:
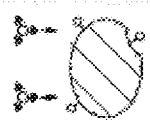
Figure 2B:
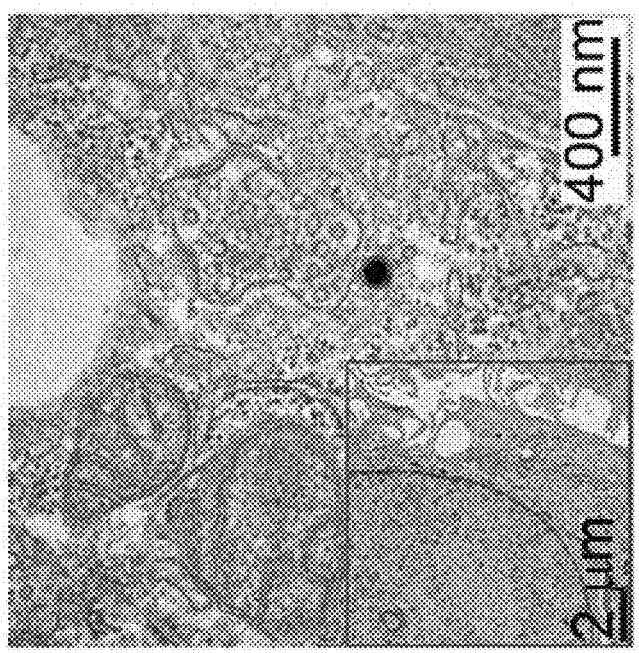
Figure 2B:
Figure 2C:
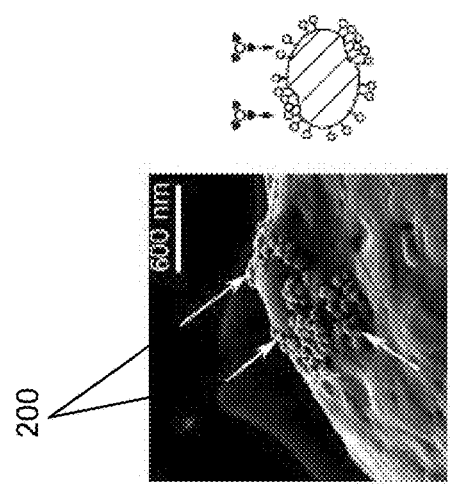
Figure 2C:
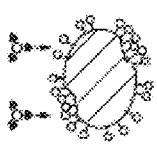
Figure 2C:
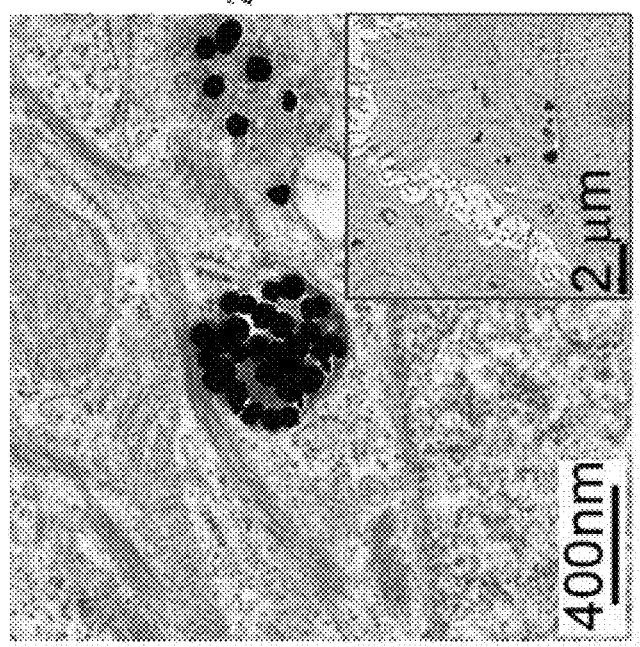
Figure 2C:
Figure 2D:
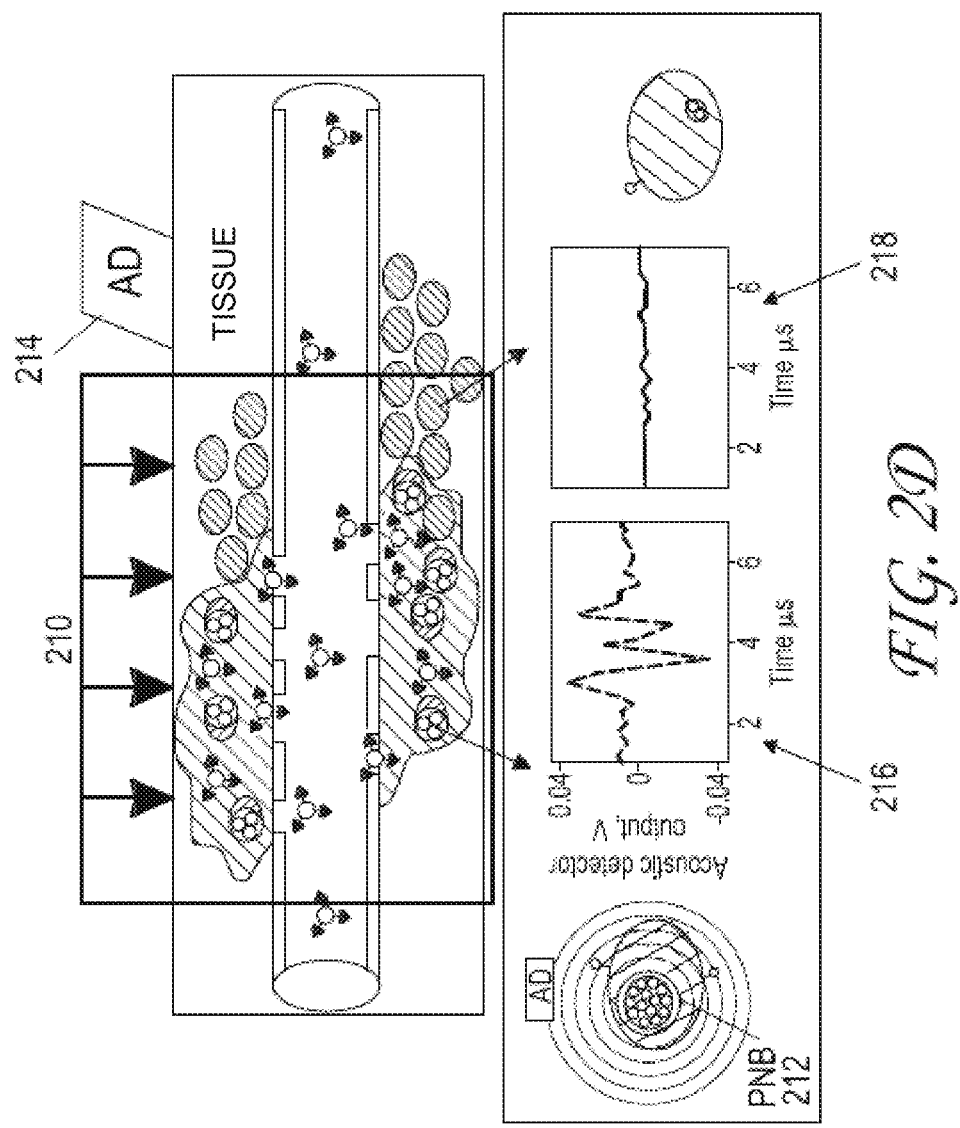

Turning to FIG. 2D, to generate PNBs, a pulsed source of electromagnetic radiation, such as a laser probe 222 can emit a single laser pulse 210 generated by a laser pulse generator 220 with wavelength between 600 nm and 1,500 nm and fluence below the PNB generation threshold for single nanoparticles but above the PNB generation threshold for their large clusters. The laser pulse can be directed against a location 224 on a patient (FIG. 2) having both normal tissue 201 and a tumor 203. In some embodiments, PNB generation threshold can be 10-15 mJ/cm$^2$ for gold-pre-treated HNSCC cells and single near-infrared laser (NIR) pulses (782 nm, 30 ps) can be used for PNB generation. An expanding and collapsing PNB 212 (FIG. 2D) can report a cancer cell by emitting a pressure pulse, which can be detected acoustically with a wide variety of detectors, such as an acoustic detector 214. The acoustic detector 214 can be any detector capable of converting a pressure pulse into optical or electrical signal, including but not limited to piezo-, fiber optical-, waveguide-based sensors of various shape and dimension, which can be applied locally to detect said pressure pulse emitted by PNB. In some embodiments, the acoustic detector 214 can include a broadband ultrasound sensor of a needle type integrated with a pre-amplifier and can be further connected to an external power supply with a second pre-amplifier. In one embodiment of the present invention, the laser probe 222 and the acoustic detector 214 can optionally be incorporated into a single probe device 230, as illustrated in FIG. 2.

With continued reference to FIG. 2D, The output of the detector or of the second pre-amplifier can be connected to a signal processing unit 224, such as a digital oscilloscope, analog-to-digital converter, other electronic devices or other types of processors, to register an acoustic time-response 216 to a single laser pulse. The acoustic time-response 216 can be displayed on a display screen 226 of the signal processor (FIG. 2). This time-response 216 from the location 224 where cancer cells might be present (the test) can be compared with a time-response previously obtained from a cancer-free location (the reference 218). As shown in the graphs in FIG. 2D, the test time-response 216 shows spikes, indicating the presence of cancer cells 204 at that location, whereas the reference time-response 218 appears relatively flat, indicating a cancer-free location. In some embodiments, the test time-response 216 and the reference time-response 218 can be placed side by side. In some embodiments, the test time-response 216 and the reference time-response 218 can be superposed on each other. An artisan will recognize from the disclosure herein other forms of the display of test time-response 216 and the reference time-response 218. The exemplary diagnostic process shown in FIGS. 2A-2D can be used at a diagnostic stage or during an onco-surgery, which will be discussed in greater detail below. The exemplary diagnostic process described herein can have the advantage of providing a surgeon during an onco-surgery with real time in vivo diagnosis. The laser pulse generator 220 can be switched on within milliseconds during a surgery. In addition, no time-consuming signal reconstruction is required (unlike photoacoustic processes) because the PNB signal amplitude is directly read from the pressure pulse signal. Single cancer cell sensitivity of the PNBs in the present disclosure (compared to that of photoacoustic, multi-spectral optoacoustic tomography and optical diagnosis processes) can result from one or more of the following: (1) the high efficacy of PNB generation by nanoparticle clusters, 10-100 fold higher than single nanoparticles, (2) much higher pressure produced by the rapid expansion and collapse of a vapor nanobubble than the thermo-elastic effect in nanoparticles employed by photoacoustic diagnosis processes, and (3) using the non-stationary PNB mechanism with a short laser pulse which provides efficient excitation of clinically safe colloidal nanoparticles with deep tissue-penetrating near-infrared laser pulse, a combination not possible in photoacoustic diagnosis processes or under stationary optical excitation. Although the diagnostic sensitivity may decrease with the tissue depth, diagnosis processes in accordance with an embodiment of this disclosure can still be capable of detecting even just about 30 residual cancer cells or less at about 4 mm or deeper, which can be equivalent to tumors below 50 um size. The high cancer cell specificity of the PNBs is based not only on the antibody-directed targeting of nanoparticles as in other diagnosis processes, but also on the cluster-threshold mechanism of PNB generation. This, in turn, can also significantly reduce the nanoparticle dose to about 1-10% of the doses employed by photoacoustic, photothermal or computer tomography diagnosis processes. Such a low nanoparticle dose can be safely delivered to the tumor. The clustering of nanoparticle conjugates with antibodies in cancer cells can generate PNBs substantially only in cancer cells with near-infrared laser pulses of low energy.

Figure 3A:
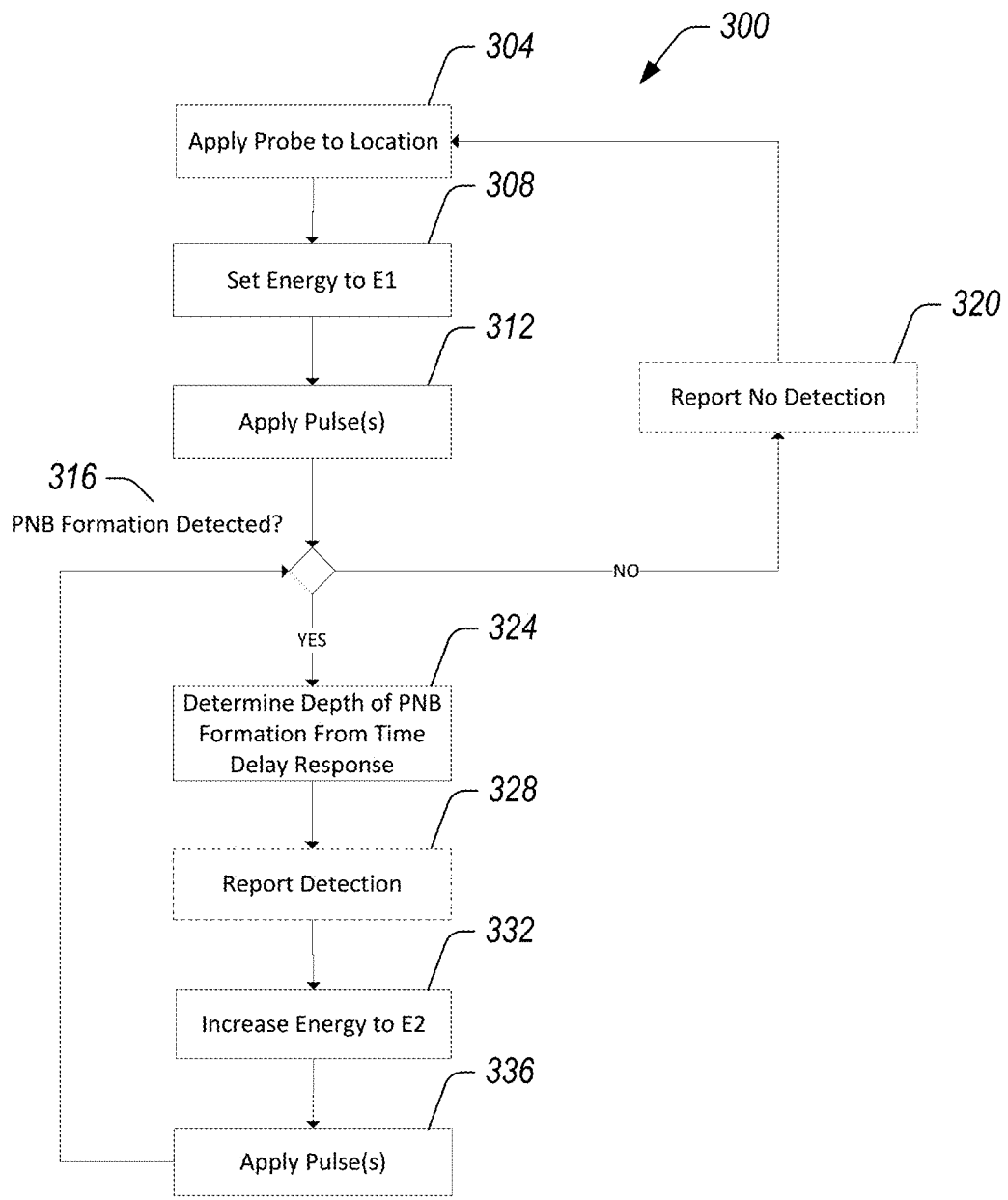
FIG. 3A illustrates an embodiment of an exemplary diagnosis process that includes a determination of a depth of cancer cells in tissue.

FIG. 3A illustrates an embodiment of an exemplary diagnosis process 300 that includes a determination of a depth of cancer cells in tissue. The process of PNB generation and detection using single pulses at a single level of laser fluence can be sufficient for diagnosis of superficial tumor or MRD in surgical margins within about 1-2 mm depth (which is better than optical processes whose sensitivity is limited by tens of micrometers of solid tissue depth for microscopic tumors or single cancer cells). To allow laser pulses to penetrate to deeper tissues, after a first laser pulse is applied to a location and a signal is read, subsequent laser pulses of increasing energy can be applied to the same location to read signals at increasing tissue depths.

For example, a plurality of laser pulses can be applied in succession at the same location on a patient, each pulse having a higher level of energy than a previous pulse to reach deeper in the tissue. As shown in FIG. 3A, a laser probe can be applied to a location on a patient at step 304. The location can be a location the probe was previously applied to, or a new location. At step 308, the laser energy can be set at E1, which can be a detection-level energy. One or more pulses of energy E1 can be applied at step 312. Applying a plurality of pulses of the same energy can ensure more thorough detection of tumor cells at substantially the same depth than a single pulse at that energy level. For example, E1 can be about 10-15 mJ/cm$^2$ in the case of gold pretreated HNSCC cells. At decision step 316, a hardware processor can determine if PNB formation has been detected in manners described herein. For example, the hardware processor can receive output of an acoustic sensor and analyze a time-delay response as described above. If PNB formation was not detected, the processor can optionally generate a report that no PNB formation or tumor cells were detected at step 320. If a positive time-delay response has been detected, the processor can determine a depth of the PNB formation, which can indicate a depth of the tumor cells or tumor-associated vasculature, from the time-delay response at step 324. The processor can optionally generate a report of detection at step 328. In some embodiments, the report of detection can include PNB formation, existence of tumor cells, or existence of tumor-associated vasculature. In some embodiments, the report of detection can include depth of PNB formation, tumor cells, or tumor-associated vasculature. At step 332, the laser energy can be set to E2, which is higher than E1. The laser energy level can be set by the processor or manually be a caregiver. Laser pulse(s) of energy E2 can be applied to the same location at step 336 in an attempt to reach tissue at a greater depth than a laser pulse of energy E1. The laser pulse(s) can be applied by the processor or manually by a caregiver.

The process as illustrated in FIG. 3A can be reliably applied since the PNB generation threshold remains substantially the same at any depth. This is because the threshold at a specific laser wavelength is determined only by the size of the nanoparticle cluster. Furthermore, cancer cells at a more superficial level of the tissue would have already responded with PNBs to previous laser pulses and the nanoparticle clusters would have been mechanically scattered by those previously-formed PNBs. In addition, single scattered nanoparticles cannot generate PNBs under the same fluence or energy level as efficiently as nanoparticle clusters. As a result, each laser pulse of higher energy can generate PNBs deeper in the tissue and for each time-response that is PNB-positive, a time delay of the laser pulse can be recorded. If a certain location in the patient's body is known or suspected to have cancer cells, multiple successive pulses, each with an increasing energy than the preceding pulse, can be applied at the same location on a patient, according to the process illustrated in FIG. 3A, until an acoustic time-response below the PNB-positive threshold is detected, indicating a cancer-free zone has been reached. The laser probe can then be directed to a new location on a patient. One of ordinary skill in the art will recognize from disclosure herein important diagnostic information relating to a size and/or a depth of the tumor from any one of, combination of any two of, or all three parameters, which can include a peak-to-peak amplitude of the PNB signal, the time delay relative to the time point of the laser pulse, and the laser pulse fluence (energy per square cm).

Figure 4C:
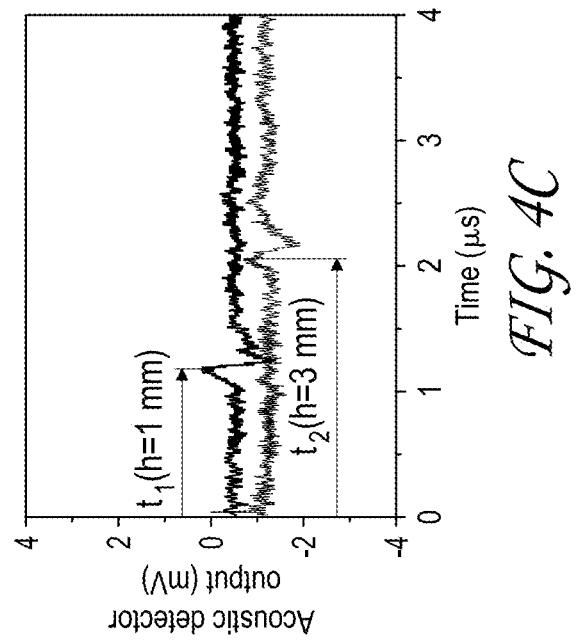
FIG. 4C illustrates an exemplary time-delay between two time-responses obtained for cancer cells at different depths.
Figure 4A:
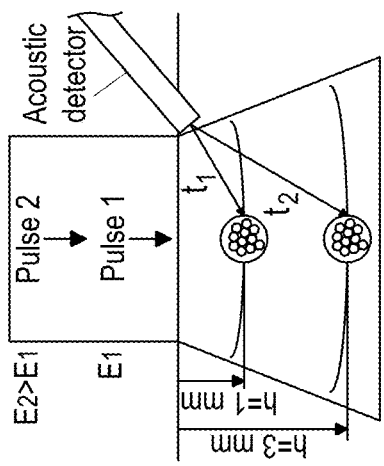
FIG. 4A illustrates an exemplary embodiment of PNB generation and detection at increasing tissue depth.
Figure 4B:
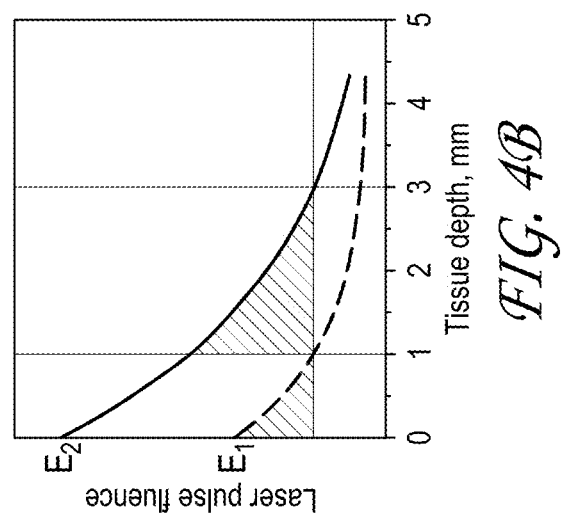
FIG. 4B illustrates exemplary laser fluence attenuation curves along tissue depth at the different entry levels of laser pulse fluence.

This multi-pulse diagnosis process can be used at a diagnostic stage or intraoperatively during an onco-surgery. At the diagnostic stage, the multi-pulse diagnosis process can inform a clinician if the tumor is superficial or subcutaneous, potentially influencing the adoption of treatment modes. In a surgery, PNBs can not only detect deeper tumors, but also indicate the depth of the tumor, thus helping a surgeon to plan the follow-up resection. Furthermore, the PNB generation depth via the time-delay from the laser pulse can be independently monitored in addition to the peak-to-peak amplitude of the PNB spike in the time-response (obtained under specific level of the laser fluence). This diagnosis process also does not require time-consuming signal reconstruction (unlike photoacoustic or tomographic diagnostic processes) because both the PNB signal amplitude and time-delay can be directly read from the primary signal (time-response). FIGS. 4A-4C illustrate an exemplary embodiment of the diagnosis process shown in FIG. 3A. As shown in FIG. 4A, two successive laser pulses, Pulses 1 and 2 can be directed at the same location. Pulse 1 can have an energy E1 and be configured to reach gold clusters, and therefore cancer cells at a depth of 1 mm. The response to the cancer cell at the depth of 1 mm can have a time delay $t_1$. Pulse 2 can have an energy E2, where E2 is greater than E1, and be configured to reach cancer cells at a depth of 3 mm. The response to the cancer cell at the depth of 3 mm can have a time delay $t_2$.

In some embodiments, the laser pulse can have a constant fluence or energy level during a diagnosis or PNB detection procedure. One or more of the following can be varied for probing cancer cells at different depths when the laser pulse is kept at the same fluence or energy level: cluster size of the nanoparticles, type of cancer-specific ligands, or a combination thereof. Cluster size of the nanoparticles formed inside the cancer cells can be controlled by varying one or more of nanoparticle composition (solid or hollow), shape, size, or a combination thereof. In this application, the size of nanoparticle may vary from about 10 nm to about 400 nm. The nanoparticles may have various shapes, including but not limited to a solid sphere, a hollow sphere, solid or hollow structures of different shape such as cube, pyramid, or irregular shape. The nanoparticles can be gold nanoparticles, or of other suitable materials, which may be chosen by a skilled artisan in view of the disclosure herein. The cancer-specific ligands in this disclosure can include but are not limited to antibody, peptide(s), aptamer(s), or any molecular ligand.

In some embodiments, a plurality of acoustic detectors can be placed at various locations around the tissue. If cancer cells are present, time-responses from the plurality of acoustic detectors can be used to provide estimated location of the cancer cells in a two-dimensional or three-dimensional manner. For example, a depth and lateral positions of the cancer cells can be estimated.

The threshold fluence for detecting the PNB can depend on the tumor and nanoparticle properties. The value of the detection threshold fluence may also be affected by levels of aggressiveness of the cancer cells. For example, a low laser pulse threshold fluence of PNB generation and detection can indicate highly aggressive cancer cells, whereas an increased threshold fluence can indicate less aggressive cells, including indolent cancer cells. This is because highly aggressive cancer cells can have a greater amount of energy available for internalizing the bioconjugated nanoparticles and therefore can form large clusters of nanoparticles inside the highly aggressive cancer cells. In contrast, less aggressive or indolent cancer cells may form medium-sized nanoparticle clusters inside these cells, and normal or non-cancer cells may only non-specifically internalize single nanoparticles. As described above, the PNB size, measured by its lifetime, can be determined by the nanoparticle cluster size. Therefore, a lower laser pulse fluence can generate a detectable PNB in the highly aggressive cancer cells. A higher laser pulse fluence can generate a detectable PNB in the less aggressive cancer cells. And a still higher laser pulse fluence can generate a detectable PNB in the normal cells. Additional details of the relationship of PNB generation threshold fluence and the aggressiveness of the cancer cells are described in Lukianova-Hleb, Ekaterina Y., et al., "On-demand intracellular amplification of chemoradiation with cancer-specific plasmonic nanobubbles," Nature medicine 20.7 (2014): 778-784, the entirety of which is incorporated herein by reference.

The lower PNB generation threshold fluence of highly aggressive cancer cells than less aggressive cancer cells can provide an advantage of using PNBs for cancer detection and removal. Specifically, in traditional forms of cancer treatment, such as chemotherapy, the highly aggressive cancer cells can be more resistant to the treatment than the less aggressive cancer cells. In the embodiments of the disclosure herein, the highly aggressive cancer cells are more susceptible to detection and destruction (see below) because a lower laser pulse fluence is required to generate PNBs in the highly aggressive cancer cells.

Figure 3B:
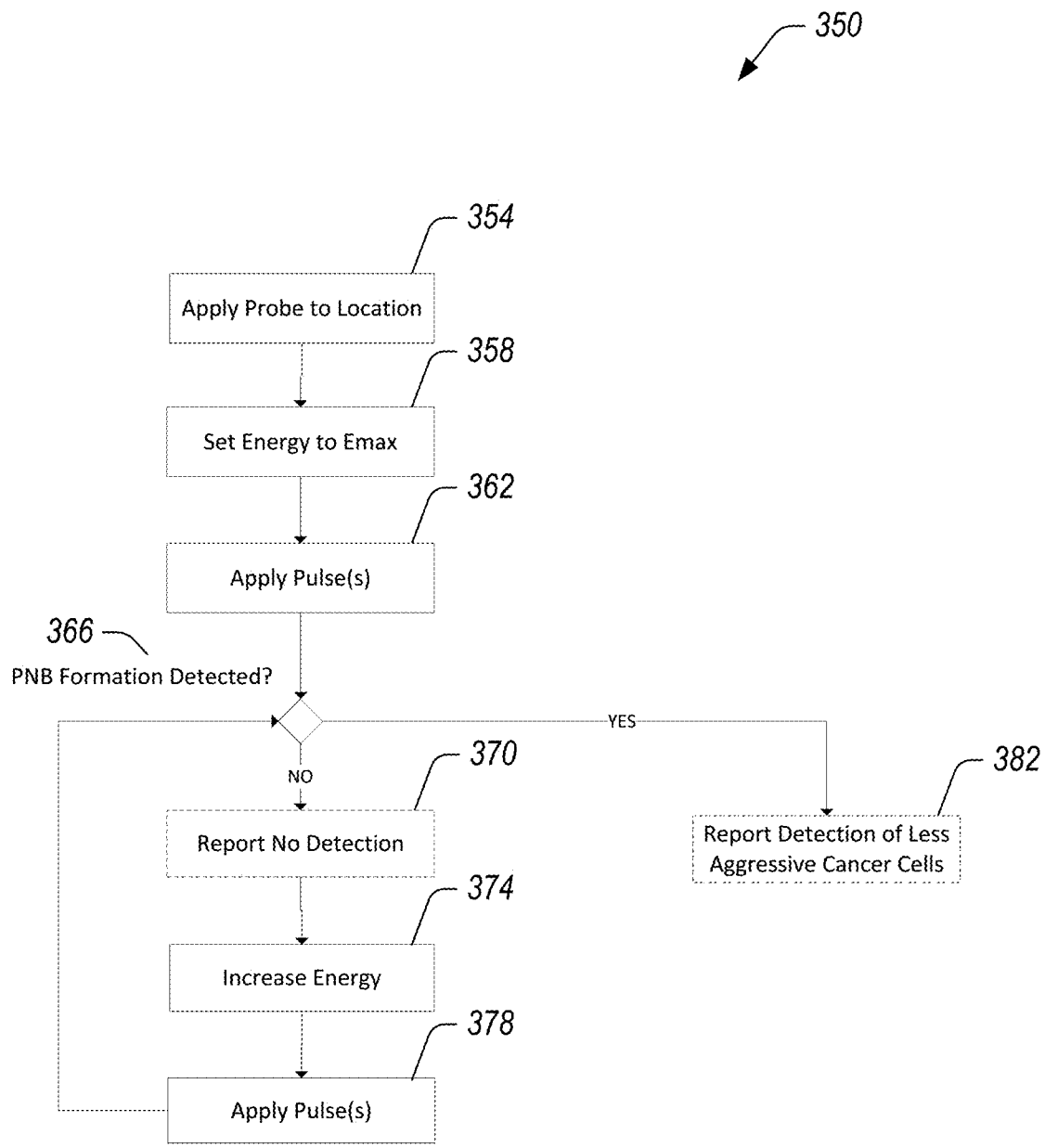
FIG. 3B illustrates an embodiment of an exemplary diagnosis process that includes a determination of aggressiveness of cancer cells in tissue.

Turning to FIG. 3B, a process 350 for determining aggressiveness of cancer cells in tissue is illustrated. Steps 354, 358, 362, and 366 can be performed in the same or similar manner as the steps 304, 308, 312, and 316 of FIG. 3A respectively. In an embodiment, in Step 358, the system can set the laser energy is $E_{max}$, which is the energy sufficient for penetrating a desired depth of the tissue at the location. When no PNB formation is detected at the decision step 366, the system can optionally report no detection at step 370. In addition, the system can increase the laser pulse energy to higher than $E_{max}$ at step 374. In an embodiment, the amount of increment can be determined based on type of suspected tumor, nanoparticle characteristics, or a combination thereof. The pulse(s) of increased energy can be applied to the same location on the patient at step 378. By increasing the energy at the same location, the system advantageously may derive information related to a measure of aggressiveness of the cancer cells. For example, in an attempt to detect presence of less aggressive cancer cells, which has a higher detection threshold fluence than the highly aggressive cancels, and detectable PNBs may not be generated at $E_{max}$ in these less aggressive cells. When PNB formation is detected with the increased energy, the system can optionally report that less aggressive cancer cells are present in step 382. If PNB formation is still not detected, the system can repeat the steps 370 (optional), 374, 378 until a predetermined endpoint energy has been applied. The endpoint energy can be determined based on type of suspected tumor, nanoparticle characteristics, or a combination thereof, and is less than the PNB generation threshold fluence of a single nanoparticle.

In some embodiments, laser pulses of a plurality of wavelengths can be applied to a location on a patient in the presence of bioconjugated nanoparticles. As described above, laser pulse wavelength for generating PNBs can depend on the type of tumor and nanoparticles. For example, PNBs of a first size can be generated in a first group of cancer cells having clusters of a first type of nanoparticles by exposure laser pulse(s) of a first wavelength, and PNBs of a second size can be generated in a second group of cancer cells having clusters of a second type of nanoparticles by exposure to laser pulse(s) of a second wavelength. In some embodiments, the first and second groups of cancer cells differ in level of aggressiveness. In some embodiments, the first and second types of cancer cells differ in types. In some embodiments, the first and second groups of cancer cells differ in both aggressiveness and types. In some embodiments, laser pulse(s) of the first and second wavelengths can be applied simultaneous to cells pre-treated with the first and second types of nanoparticles. If both the first and second groups of cancer cells are present, a synergistic PNB that is greater in size than a summation of the first and second sizes can be detected. If only one of the first and second groups of cancer cells are present, only the PNB of the first or second size can be detected. In some embodiments, laser pulses of more than two different wavelengths can be applied simultaneous to cells pretreated with more than two types of nanoparticles. This mechanism, also called a "rainbow" mechanism, can be configured to detect cancer cells of various types, levels of aggressiveness, or both. Additional details of the rainbow mechanism are described in Lukianova-Hleb, Ekaterina Y., et al., "Tunable plasmonic nanoprobes for theranostics of prostate cancer," Theranostics 1 (2011): 3-17, the entirety of which is incorporated herein by reference.

An artisan will recognize from the disclosure herein that by manipulating some or all of the energy levels of one or more laser sources, the wavelengths of one or more radiation pulses, the size, type, shape, composition, construction or the like of the nanoparticles, the method of delivery of the same to the patient, or the specific methodology of applying the laser pulses, the system may electronically determine and report a wide variety of useful information to a caregiver, including existence, location, or depth of unwanted tissue, type of unwanted tissue, or characteristics of the unwanted tissue including a measure of aggressiveness, and the like.

Figure 5:
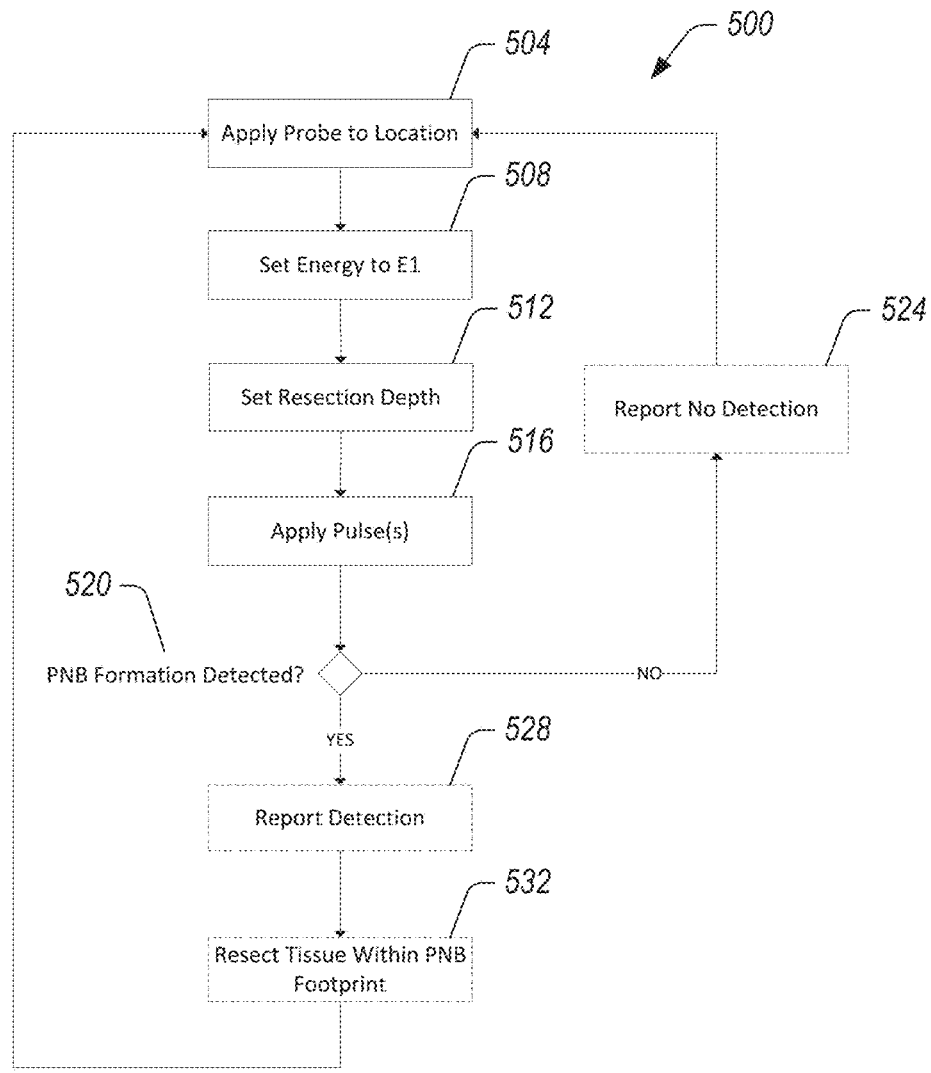
FIG. 5 illustrates an exemplary surgical process for managing a resectable MRD.
Figure 6:
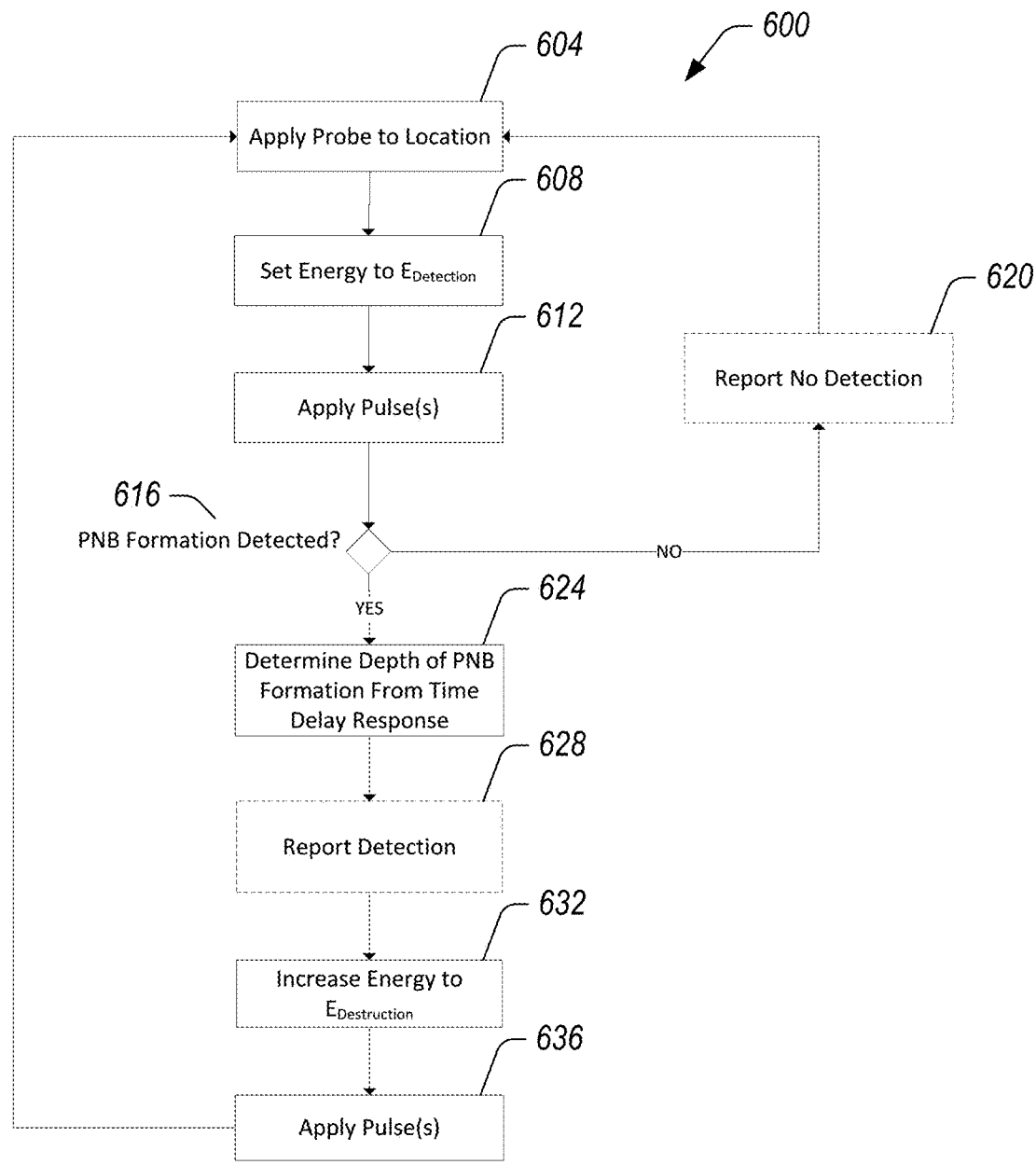
FIG. 6 illustrates an exemplary surgical process for managing an unresectable MRD.

FIGS. 5 and 6 illustrate an exemplary surgical process for resectable and unresectable MRD. In managing either resectable tumor or unresectable tumor, the surgeon may perform a primary resection of the tumor before applying a diagnosis process described above and shown in FIGS. 2 and 2A-4C. With either the single-pulse or the multi-pulse diagnosis process, a PNB-positive time-response can be interpreted as MRD in a surgical bed within a PNB-positive zone as defined by a footprint of a PNB probe. Tissue within the PNB-positive zone can then be eliminated by a macro-surgical local resection tool 228 (FIG. 2) if the tumor is resectable, or through PNB nano-surgery if the tumor or MRD cannot be resected.

More specifically, FIG. 5 illustrates an exemplary surgical process 500 for resectable MRD. After the primary resection in a specific location, a PNB probe, that is a probe emitting laser pulses with wavelength and duration in the ranges described above, can be applied to the same location at step 504. In some embodiments, the laser probe can be applied to a new location. At step 508, the laser energy can be set at E1, which can be a detection-level energy. At step 512, a resection depth can be set. In some embodiments, the resection depth can calculated as a function of a maximum depth that a laser pulse of energy E1 can penetrate. In some embodiments, the resection depth can be manually set, for example, at 1 mm. One or more pulses of energy E1 can be applied at step 516 to determine if there are residual tumor cells after the resection. Applying a plurality of pulses of the same energy can ensure more thorough detection of tumor cells at substantially the same depth than a single pulse at that energy level. At decision step 520, a hardware processor can determine if PNB formation has been detected in manners described herein. For example, the hardware processor can receive output of an acoustic sensor and analyze a time-delay response as described above. If PNB formation was not detected, the processor can optionally generate a report that no PNB formation or tumor cells were detected at step 524. If a positive time-delay response has been detected, the processor can optionally generate a report of detection at step 528. In some embodiments, the report of detection can include PNB formation, existence of tumor cells, or existence of tumor-associated vasculature. In some embodiments, the report of detection can include depth of PNB formation, tumor cells, or tumor-associated vasculature. At step 532, tissues within a PNB footprint can be resected.

The procedure at the step 536 can be a standard "macro" surgery using the macro-surgical resection tool 228 (FIG. 2), which can be operated by either a surgeon or a robotic arm, to resect each PNB-positive zone (the probe footprint). A PNB-positive zone may have a depth of about 0-30 mm, or about 0.5-5.0 mm, a length of about 1-20 mm or about 1-10 mm, and a width of about 1-20 mm, or about 1-10 mm. For example, a PNB-positive zone can be 1 mm in depth×3 mm in length×3 mm in width. One of ordinary skill in the art would recognize from the disclosure herein other dimensions suitable for the PNB-positive zone. Follow-up control of the MRD can include applying the PNB probe again to the same location and collecting another time-response. In some embodiment, the PNB probe can emit a laser pulse of the same energy as the preceding pulse before resecting the PNB-positive zone. In the case of a PNB-positive signal, the procedure can be repeated and a PNB-positive zone can be resected each time in a loop of "detect PNB—resect—detect PNB" until the time-response reports no PNBs. In an embodiment of the present invention, options are available in the case of a PNB-negative signal from the first single laser pulse. One option is to move the PNB probe to a new location. Another option is to incise tissue in the footprint of the PNB probe to ensure removal of residual cancer cells at a margin of the primary section and to the depth corresponding to the depth of the PNB generation and detection. Yet another option is to apply additional pulses of increasing energy levels to reach deeper into the tissue. A person of ordinary skill in the art will recognize from the disclosure herein still other options. In one embodiment, a caregiver chooses from the three options. In another embodiment, a computer program chooses from the options by comparing the time-response with a threshold or a look-up table. The PNB-guided "macro" surgical process is in line with an objective of minimizing the volume of resected margins when eliminating MRD. Compared to standard surgery without the aid of the PNB technology, this PNB-guided surgical process can reduce the resected volume from a relatively large (for example, 10 mm deep×10×10 mm) to a small one (for example, 2 mm deep×3×3 mm). In some embodiments, the reduction in the resected volume can be about 50-fold. Thus, the PNB-guided surgical process can spare adjacent important structures and make surgery less morbid. For example, in head and neck surgery, in order to avoid MRD in the tongue, a surgeon removes most of the tongue first, and then does reconstructive surgery to restore the tongue with donor tissues. With PNB-guided "macro" surgical process, this morbid step can be optimized without compromising the outcome, thus improving both the patients' eligibility for surgery and their quality of life. The diagnostic process of this surgical process described herein can take only microseconds for each measurement and does not limit the surgical procedure. In clinic, PNB-guided macro-surgery can be integrated into manual, endoscopic or robotic surgery by using a standalone PNB probe or integrating it with surgical endoscope or robotic arm to provide detection and elimination of MRD in solid tissue in surgical bed in seconds.

FIG. 6 illustrates an exemplary surgical process called a PNB nano-surgery 600 for unresectable MRD. When a tumor or MRD grows along an important nerve or an artery, even PNB-guided macro-surgery as shown in FIG. 5 can be too risky. Upon detecting a PNB-positive time-response using the diagnosis process described herein at a location that is deemed unresectable by the surgeon, the cancer cell-specific mechanical impact of the PNB can be used to eliminate the cancer cells. Specifically, after the primary resection in a specific location, a PNB probe can be applied to the specific location on a patient at step 604. In some embodiments, the location can be a new location. At step 608, the laser energy can be set at a detection-level threshold fluence $E_{Detection}$. One or more pulses of $E_{Detection}$ can be applied at step 612. Applying a plurality of pulses of the same energy can ensure more thorough detection of tumor cells at substantially the same depth than a single pulse at that energy level. For example, $E_{Detection}$ can be about 10-15 mJ/cm$^2$ in the case of gold pretreated HNSCC cells. At decision step 616, a hardware processor can determine if PNB formation has been detected in manners described herein. For example, the hardware processor can receive output of an acoustic sensor and analyze a time-delay response as described above. If PNB formation was not detected, the processor can optionally generate a report that no PNB formation or tumor cells were detected at step 620. If a positive time-delay response has been detected, the processor can determine a depth of the PNB formation, which can indicate a depth of the tumor cells, from the time-delay response at step 624. The processor can optionally generate a report of detection at step 628. The processor can also optionally generate a report of the depth of PNB formation at step 632. In some embodiments, the report of detection can include PNB formation, existence of tumor cells, or existence of tumor-associated vasculature. In some embodiments, the report of detection can include depth of PNB formation, tumor cells, or tumor-associated vasculature. The laser energy can then be then be set to a cell destruction threshold fluence $E_{Destruction}$, which is higher than $E_{Detection}$, at step 632. The laser energy or fluence level can be set by the processor or manually be a caregiver. Laser pulse(s) of $E_{Destruction}$ can be applied to the same location at step 636 in an attempt to collapse or explode the PNBs, which can destroy the unresectable or residual tumor cells in which the PNBs reside. The laser pulse(s) can be applied by the processor or manually by a caregiver.

In the case of a PNB-positive time-response, the same location where the PNB-positive time-response was detected can be exposed to additional laser pulses of $E_{Destruction}$, for example, at about 40 to 400 mJ/cm$^2$, to cause destruction of the detected cancer cells by explosive effect of the PNBs. In some embodiments, laser pulses at maximal safe energy can be applied to cause maximal destruction of detected residual cancer cells by PNBs without affecting neighboring healthy tissues. The PNB nano-surgery can also be monitored in real time via the PNB signals using the diagnosis process described above and the "detect PNB-nanosurgery-detect PNB" loop can be repeated until the time-response reports no PNBs (indicating all cancer cells have been destroyed).

In an embodiment of the present invention, options can be available in the case of a PNB-negative signal from the first single laser pulse. One option is to move the PNB probe to a new location. Another option is to apply cell destruction-level laser pulse fluence to ensure removal of residual cancer cells at a margin of the primary section. Yet another option is to apply additional pulses of increasing energy levels to reach deeper into the tissue. A person of ordinary skill in the art will recognize from the disclosure herein still other options. In one embodiment, a caregiver chooses from the three options. In another embodiment, a computer program chooses from the options by comparing the time-response with a threshold or a look-up table. For unresectable therapy-resistant tumors or MRD, the PNB-induced selective mechanical destruction of residual cancer cells not only improves the surgical outcome, but can also replace toxic chemo- and radiation therapies, thus improving the quality of patients' life and making surgical treatment possible for currently ineligible patients.

Tumor Micro Environment (TME) Detection & Elimination

Figure 17A:
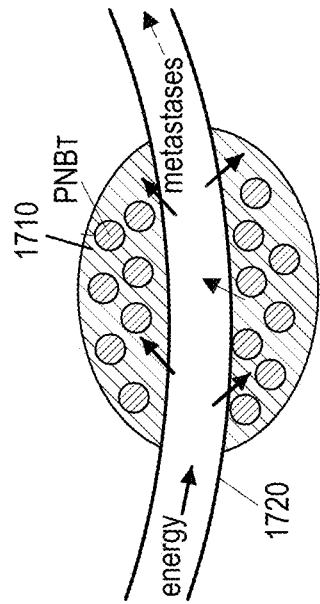
FIGS. 17A-D illustrate exemplary cancer cells and/or TME detection and elimination system in accordance with an embodiment of the disclosure.

Cancer cells can sometimes survive even after the macro- and nano-surgery described herein. The tumor micro-environment ("TME") can also survive with these cancer cells. The TME can include non-tumor targets that are biologically associated with a tumor, such as tumor-specific blood vasculature and other components that are understood by one of ordinary skill in the art. As shown in FIG. 17A, the tumor-specific vasculature 1720 can supply and support the growth of any tumor cells 1710 that survived a macro- or nano-surgery, causing local recurrence of tumor. In addition, blood flow in the tumor-specific vasculature 1720 can also bring tumor cells to other locations in the patient's body, resulting in metastases.

Figure 17B:
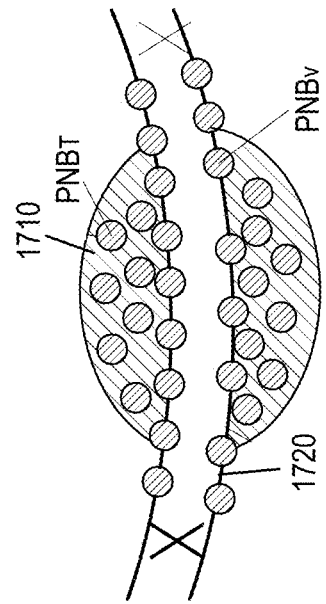
Figure 17C:
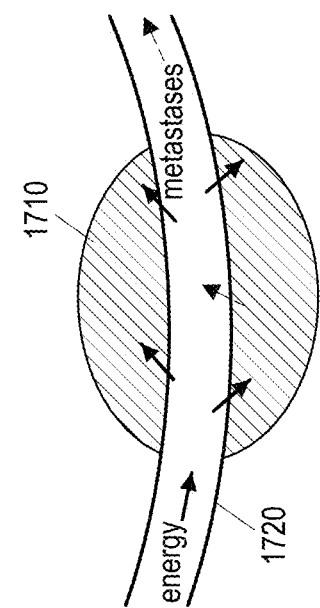

Embodiments of TME detection and elimination using the PNB technology will now be described using tumor-specific vasculature as an example, although a skilled artisan will understand from the description herein that the embodiments of TME detection and elimination disclosed herein can be applied to any type of TME. Tumor-specific vasculature can differ from normal blood vessels, such as by expressing on the wall of the vessel tumor-specific receptors. Examples of tumor-specific receptors on the vessel wall can include VEGF-A, VCAM-1, avb3 integrins, and the like. By administrating nanoparticles conjugated to the vascular-specific ligand that target these receptors, the PNB technology described above for detecting and eliminating cancer cells can be used to detect and eliminate the tumor-specific vasculature. More specifically, as shown in FIG. 17B, gold conjugates can be systemically administered and $PNB_T$ can form in the tumor 1710. As shown in FIG. 17C, $PNB_V$ can form on the epithelial wall of the tumor-specific vessel 1720. In some embodiments, the same gold conjugate with the same ligands configured for formation of $PNB_T$ can be configured for forming $PNB_V$. In other embodiment, vasculature-specific gold conjugates and ligands can be used for generating $PNB_V$. In some embodiment, gold spheres of 240 nm can be used for the generation of PNBs on the epithelial wall of the tumor-specific vasculature under excitation with a 1064 nm laser pulse. In some embodiment, gold spheres of 60 nm can be used for the generation of PNBs on the epithelial wall of the tumor-specific vasculature under excitation with a 782 nm laser pulse.

The process as illustrated in FIG. 6 and described above can be applied for detection and destruction of the tumor-specific vasculature. After application of laser pulse(s) for $PNB_V$ generation or tumor-specific vasculature detection, laser pulse(s) of a higher energy sufficient for destruction of the vasculature by the explosive impact of the $PNB_V$ can be applied. The PNB-induced destruction of the tumor-specific vasculature and disruption of the blood supply and flow may additionally destroy residual cancer cells that survived a macro- or nano-surgery by mechanical impact due to explosive effect of the PNBs. As described above, the destruction of the tumor-specific vasculature can further improve cancer treatment by reducing the possibility of the local recurrence by cutting off the energy or nutrient supply to residual local cancer cells. The destruction of the tumor-specific vasculature can also reduce the possibility of remote metastases from the target tumor by removing the channel for the residual cancer cells to travel to other parts of the patient's body.

Combination of Cancer Cell and TME Detection and Elimination

Figure 17D:
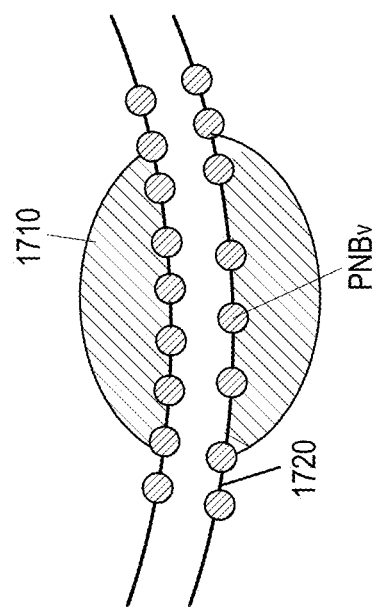

In some embodiments, in addition to using the PNB-induced destruction of the TME as a stand-alone treatment, the PNB-induced destruction of the tumor-specific vasculature and disruption of the blood supply and flow can be an intra-operative adjuvant treatment to the direct treatment of unresectable/residual tumors. As shown in FIG. 17D, $PNB_T$ can form in the tumor 1710 and $PNB_V$ can also form on the epithelial wall of the tumor-specific vessel 1720 at the same time or in one treatment with laser pulses. That is, gold conjugates can be administered to both the cancer cells and the tumor-specific vasculature to generate both $PNB_T$ and $PNB_V$. In some embodiments, the same gold conjugate with the same ligands configured for formation of $PNB_T$ can be configured for forming $PNB_V$. In other embodiment, vasculature-specific gold conjugates and ligands can be used for generating $PNB_V$. In some embodiments, the same gold conjugate with the same ligands can be used to form the $PNB_T$ and $PNB_V$. In other embodiment, tumor-specific gold conjugates or ligands can be used for generating $PNB_T$ and vasculature-specific gold conjugates or ligands can be used for generating $PNB_V$. Although the combination of cancer cell and TME detection and elimination are described using tumor-specific vasculature as an example, a skilled artisan will understand from the description herein that these embodiments can be applied to any type of TME.

The process as illustrated in FIG. 6 and described above can be applied for detection and destruction of the cancer cells, and the tumor-specific vasculature (if present). In some embodiments, the same detection-level energy laser pulse(s) can be applied to form both the $PNB_T$ and $PNB_V$ in the cancer cells and the tumor-specific vasculature respectively. In other embodiments, laser pulse(s) of different detection-levels energy can be used to form the $PNB_T$ and $PNB_V$. After application of laser pulse(s) for generating the $PNB_T$ and $PNB_V$, if tumor, or tumor-specific vasculature, or both are present, laser pulse(s) of a higher energy sufficient for destruction of the tumor cells and the tumor-associated vasculature by the explosive impact of the $PNB_T$ and $PNB_V$ can be applied. In some embodiments, the same higher energy laser pulse(s) can be applied to collapse both the $PNB_T$ and $PNB_V$, leading to destruction of both the cancer cells and the tumor-specific vasculature substantially simultaneously. In other embodiments, laser pulse(s) of different levels of higher energy can be used to collapse or explode both the $PNB_T$ and $PNB_V$. The PNB-induced destruction of the tumor-specific vasculature and disruption of the blood supply and flow may destroy additional cancer cells by mechanical impact due to explosive effect of the $PNB_V$. Targeting and destroying both the tumor and the tumor-specific vasculature can further improve the surgical outcome. For example, the combination of PNB-assisted removal of tumor and TMD can achieve about 5-10 fold improvement in overall survival compared to standards of care.

EXAMPLES

Examples of aspects of the embodiments of the present disclosure will now be described. More details of aspects of the embodiments of the present disclosure are provided in Appendices A and B.

Example 1: Cancer Models and Characterization

Figure 7:
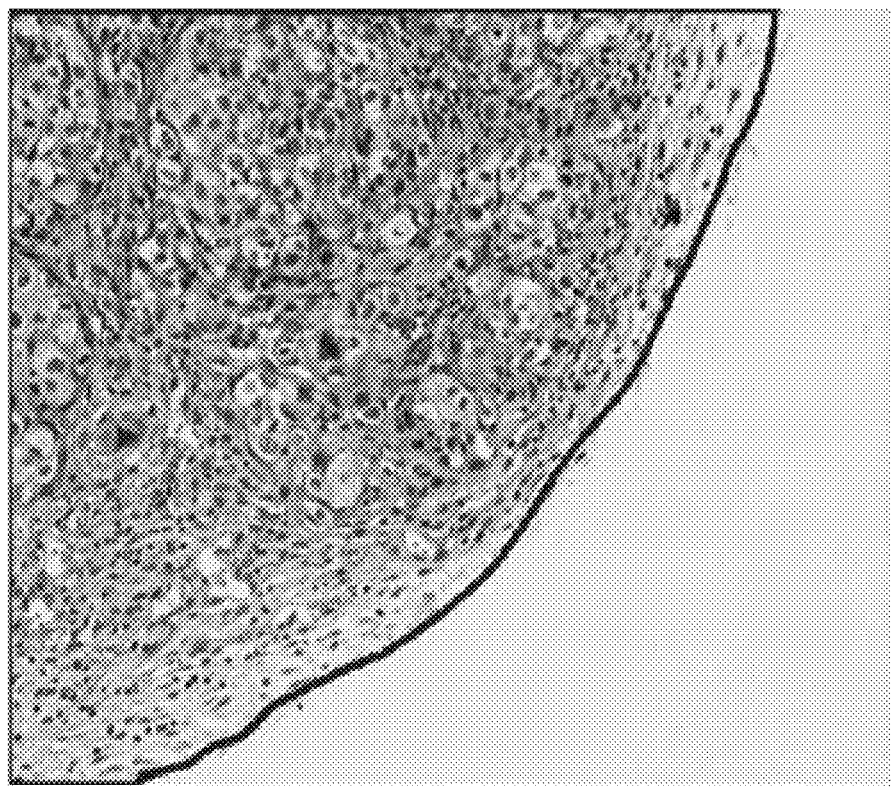
FIG. 7 illustrates an exemplary histological image of a resected primary tumor.

HNSCC is a very aggressive and lethal cancer whose surgery is challenged by resectable and unresectable MRD which later often cause lethal local recurrence. This cancer was modelled with aggressive and resistant HN31 cells obtained from J. Myers' laboratory, UT MD Anderson Cancer Center (Houston, TX) and tested for *Mycoplasma* contamination before their use. HNSCC overexpress Epidermal Growth Factor Receptor, against which there is a clinically-approved antibody, Panitumumab. Four cancer models of increasing complexity were used. To verify acoustic detection of PNBs, intact or gold conjugate-pretreated HNSCC cells in transparent media (model 1) were used. To study acoustic detection of cancer cells in solid tissue (model 2), a precise amount of gold conjugate-pretreated cancer cells was injected into a specific depth of a chicken breast with a nano-syringe. In the 3rd, in vivo model (model 3), pretreated and intact cancer cells were similarly injected into the surgical bed of anesthetized mice (athymic nude, strain CRL-490, 6 weeks age). To study the intraoperative detection and elimination of MRD (model 4), a deeply-seeded xenograft HNSCC tumor was established in the mouse. The tumor was grown to 5-6 mm size to ensure its infiltration into the normal tissue underneath and to achieve a mature vascularization (important for the systemic delivery of gold conjugates). To establish MRD intraoperatively, the tumor was grossly resected using aseptic surgery. The nest of the resected primary tumor was considered to have MRD as had been verified previously by observing almost 100% local recurrence after resecting the primary tumor. The area of the surgical bed outside a >3 mm margin around the tumor nest was considered as MRD-negative location. Presence of MRD after resection of the primary tumor was confirmed with standard pathology, such as H&E staining in FIG. 7 and later by observing local recurrence. After the PNB and surgical procedures in MRD-positive and -negative locations were completed, the wound was closed and the animal was monitored for local tumor recurrence and overall survival. The cancer metrics that were used include: (1) the number of injected cells in the 2nd and 3rd models, while in the 4th model, (2) the volume of the recurrent tumor was used, and (3) the animal overall survival time after surgery. Six animals were used for groups 1 and 2 and five animals for group 3. Animals were euthanized when the size of the recurrent tumor reached 10 mm, which was set as the moribund threshold. Animal group sizes were set to support statistically valid data and to minimize animal use. Animals were randomly assigned to groups for the experiments. These studies were not blinded since the same investigators performed the grouping, dosing and analyses, rendering it unfeasible. Animals were used according to Animal Care Use Guidelines under the protocols approved by the Institutional Animal Care and Use Committees of Rice University and Houston Methodist Research Institute.

Example 2: Gold Targeting and Clustering

To form in vivo intracellular clusters of gold colloids as PNB sources, several universal and previously verified mechanisms were used: leaky tumor micro-vasculature and the small size of the gold colloid conjugates (60 nm spheres) enable them to reach the tumor with the help of an effect called "enhanced permeability and retention" as shown in FIG. 2A, which prompts the receptor-antibody based accumulation of gold conjugates at the surface of cancer cells as shown in FIG. 2B, and finally the receptor-mediated endocytosis of gold conjugates as shown in FIG. 2C. This is endocytosis, the universal cell defense mechanism, which internalizes gold nanoparticles and concentrates them into clusters in endo-lysosomal compartments as shown in FIG. 2C, as was found earlier in vitro and in vivo. This mechanism, which efficiently differentiates cancer and normal cells by forming the largest gold clusters only in cancer cells (FIG. 2C), was also verified in vivo for HNSCC: while tumor-average cluster size was around 300 nm (equivalent of tens of aggregated 60 nm nanoparticles) the adjacent normal tissue yielded only 64 nm (equivalent of single nanoparticles). The increase in size of the gold cluster provides the selective generation of PNBs in HNSCC cells because the PNB generation threshold fluence rapidly decreases with the cluster size (see the PNB sections below for details). The clustering mechanism is sensitive to the nanoparticle diameter: larger particles (>100 nm) cannot be easily internalized by cancer cells and therefore cannot create intracellular clusters. Smaller particles (<10 nm) are rapidly cleared by the organism and therefore cannot efficiently accumulate in the tumor.

The low doses of gold colloids employed are associated with negligible systemic toxicity. 60 nm spheres (NanoComposix, Inc, San Diego, CA) were used to covalently conjugate (VanPelt Biosciences LLC (Ijamsville, MD)) to the clinically-approved anti-Epidermal Growth Factor Receptor antibody, Panitumumab (Vectibix, Amgen Inc., Thousand Oaks, CA). This antibody is used in clinic against HNSCC. To form gold clusters in vitro, gold conjugates were incubated with cells for 24 h under physiological conditions at the concentration of gold conjugate suspension corresponding to the optical density of 0.08 (measured at the maximum of the optical spectrum as shown in FIG. 8A). This corresponds to a dose of approximately 0.7 µg/ml. To form gold clusters in vivo, gold conjugates were systemically administered intravenously at the low dose of 4 mg/kg body weight 24 hours prior to the optical excitation, in order to allow their efficient clustering in the tumor. This dose is only 1-10% of those reported for the diagnostic and therapeutic doses of gold nanoparticles in vivo. These doses, timing and administration protocol were achieved as a result of several optimization experiments focused on the efficient clustering of gold nanoparticles in tumors:

A. The gold clustering efficacy was quantified through four independent metrics and methods: (1) by measuring the level of gold in tumors and other organs (which were harvested at a specific time, 6-72 h, after the systemic administration of gold conjugates) with inductive-coupled plasma mass-spectroscopy (ICP-MS); (2) by directly measuring the size of gold clusters in harvested tissues with transmission electron microscopy; (3) by measuring PNB lifetime (the metric of the maximal diameter of PNB which correlates with the cluster size) in slices of the harvested tissue, and (4) by measuring the acoustic amplitude of PNB time-responses in vivo. It was found that the systemic administration of gold nanoparticle conjugates is preferable to their local injection and results in tumor-specific clustering in vivo. In addition, it was found that 60 nm gold spheres provide the best generation of PNBs in HNSCCC in vivo compared to smaller nanoparticles. It is difficult for cells to internalize nanoparticles >100 nm. With the above methods, it was determined that efficient clustering in vivo requires at least 24 hours of lead time after the systemic injection of gold conjugates.

Figure 9A:
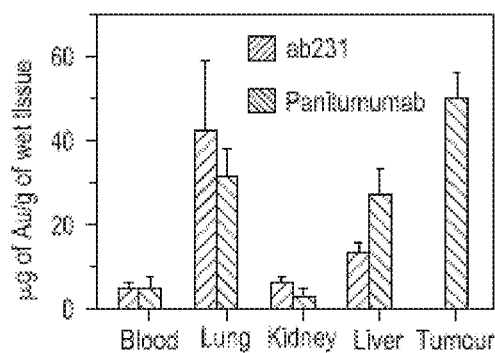
FIG. 9A illustrates exemplary biodistributions of gold conjugates with human antibodies in nude mice and gold conjugates with mouse antibodies in normal mice.

B. To optimize systemic targeting, the previous measurements were amended with the ICP-MS (Perkin Elmer Nexion 300 ICP-MS, Perkin Elmer, Inc., Waltham, MA) evaluation of the gold accumulation in tumors and other organs as a function of:

The organ: tumor, lung, liver, kidney and blood (FIG. 9A);

The targeting antibody (FIG. 10A): active targeting, compared to passive targeting (gold without antibody) is important for efficient systemic targeting.

The size of the primary tumor (FIG. 10B): the tumor stage determines the level of tumor vasculature in a xenograft model, and it is the vasculature which delivers gold to a tumor. In the case of MRD detection, tumors are usually mature enough, and this ensures the efficient systemic delivery and accumulation of gold under active targeting with an HNSCC-specific antibody.

The interaction of the targeting antibody with the immune system. To ensure the clinical translation of gold conjugates, the anti-Epidermal Growth Factor Receptor antibody "liver sink" effect (which is associated with clinical challenges in using such antibodies) and the safety of gold in vivo were additionally studied. A normal mouse with an active immune system was identically treated with gold conjugated to anti-mouse EGFR antibody. The gold biodistribution (FIG. 9A) was similar to that obtained in the xenograft model and human antibody (Panitumumab). Thus, gold conjugates (unlike the antibody alone) did not reveal a significant liver sink effect and therefore can be administered in clinic at a relatively low dose.

As a result of this optimization, the following optimal combination was determined: primary tumors should be above 5 mm, and Panitumumab antibody should be used to target gold, 24 hours are required to achieve clustering, and 60 nm gold spheres at a dose of 4 mg/kg.

Example 3: Safety of Gold Nanoparticles In Vivo

Figure 9H:
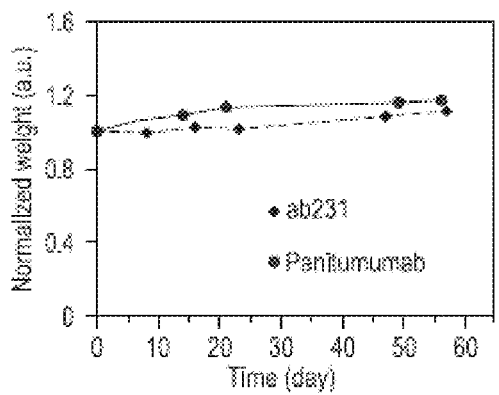
FIG. 9H illustrates an exemplary body weight as a function of time for mice with no injection of gold conjugates and mice after systemic injection of gold conjugates.
Figure 9B:
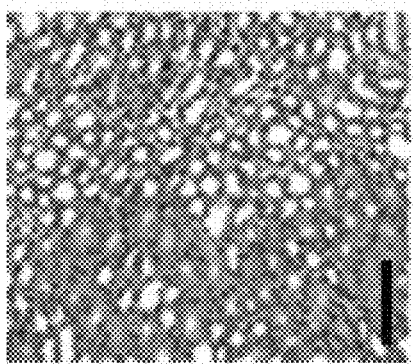
FIG. 9B is an exemplary histological analysis of a liver obtained from an animal that was not administered gold conjugates.
Figure 9C:
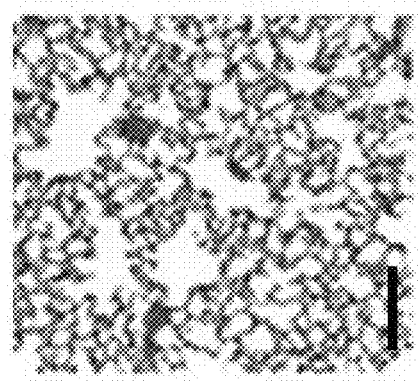
FIG. 9C is an exemplary histological analysis of a lung obtained from an animal that was not administered gold conjugates.
Figure 9D:
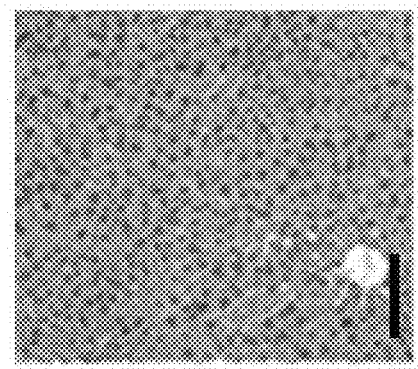
FIG. 9D is an exemplary histological analysis of a kidney obtained from an animal that was not administered gold conjugates.
Figure 9E:
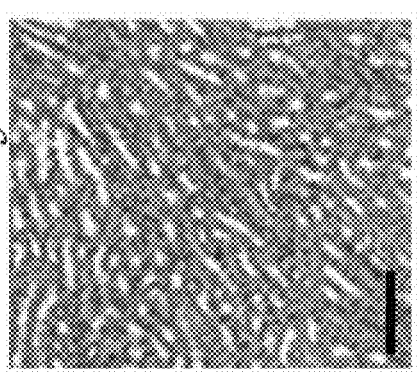
FIG. 9E is an exemplary histological analysis of a liver obtained from an animal 72 h after administration of gold conjugates.
Figure 9F:
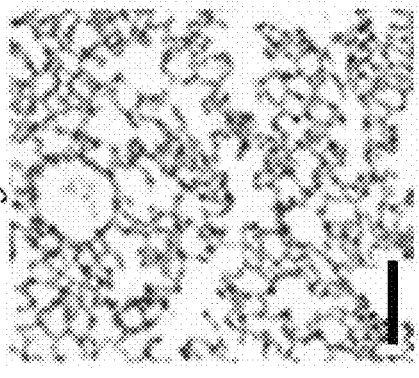
FIG. 9F is an exemplary histological analysis of a lung obtained from an animal 72 h after administration of gold conjugates.
Figure 9G:
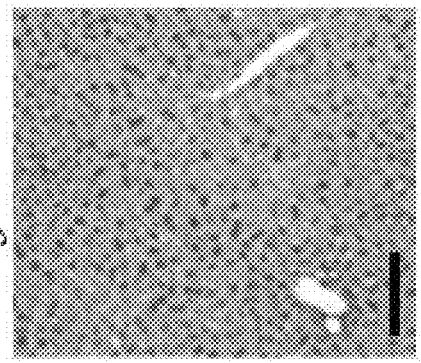
FIG. 9G is an exemplary histological analysis of a kidney obtained from an animal 72 h after administration of gold conjugates.

The toxicity of gold conjugates in vivo has been measured short term (24 and 72 h after administration) and long term (over 1 month). Three animals were studied for each time-point. To determine short-term toxicity, the harvested liver, kidney, spleen and lung were analyzed for necrosis, apoptosis and other standard signs of toxicity via standard pathology. The harvested organs (kidney, lung, liver, heart) were placed in 10% neutral buffered formalin and fixed for up to 48 hours. Organs were then processed routinely and coil sections were stained with hematoxylin and eosin (H&E). Sections were examined by a board certified veterinary pathologist. Regions of normal tumor/organ and necrotic tumor/organ were delineated. The metric of tissue damage was the % of necrosis, defined as the ratio of the area of grossly necrotic tissue to the total area of tissue in a given section. Long-term toxicity was monitored by measuring animal weight and behavior. More sophisticated methods were not applied because the gold nanoparticles and their low doses used were safe: no signs of toxicity were observed for the period >2 months. The short- and long-term toxicity in vivo was verified. The histological evaluation of organs harvested at 24 h and 72 h from intact and gold-treated mice (FIGS. 9B-9G) revealed no toxic effects of the gold, as shown in Table 1 below. Based on the high safety of the gold, the long-term toxicity was analyzed only by monitoring the body weight and animal behavior (two standard parameters) in intact and gold-treated mice and also revealed no adverse effects (FIG. 9H). Therefore, the gold conjugates, doses, and the systemic targeting method employed were safe in vivo and provided efficient delivery of the gold conjugates to and their clustering in a tumor to support tumor-specific PNB generation in vivo.

TABLE 1

Short-term toxicity of treatment
(defined as % of grossly necrotic area / total examined area)

| Treatment | Time | Kidney | Liver | Lung |
|---|---|---|---|---|
| Untreated | 24 h | 0% | 0% | 0% |
|  | 72 h | 0% | 0% | 0% |
| PNB | 24 h | 0% | 0% | 0% |
|  | 72 h | 0% | 0% | 0% |

Example 4: Plasmonic Nanobubble (PNB) Generation

PNBs were generated around clusters of gold spheres with single near-infrared laser (NIR) pulses (782 nm, 30 ps, Ekspla PL2251/OPG03, Ekspla UAB, Lithuania). As shown in FIG. 8A, optical absorbance under stationary optical excitation peaks between 500 and 600 nm and is negligible at 782 nm. While the stationary optical excitation of gold spheres in near-infrared is not efficient due to their low optical absorbance in this spectral interval, the non-stationary optical excitation method described herein provides efficient PNB generation around these nanoparticles with a 30 ps laser pulse at NIR wavelength of 782 nm, the wavelength associated with minimal bio-damage and maximal tissue penetration depth. Due to the transient photothermal modification of the nanoparticle surface by a short NIR laser pulse, the PNB generation efficacy at 782 nm reaches the level achieved by excitation at the visible wavelength (FIG. 8B). Unlike any nanoparticle, a PNB is a non-stationary transient event, an expanding and collapsing vapor nanobubble of nanosecond duration, usually without recoil. Such a nanobubble results from the rapid evaporation of the liquid around an overheated gold cluster due to the absorption and plasmonic conversion of the laser pulse energy. The use of a nanoparticle cluster instead of single nanoparticles or their ensembles provides a significant reduction in the threshold laser fluence of the PNB generation and an increase in the PNB generation efficacy because the threshold fluence decreases with the cluster size. This unique property of PNB, in turn, provides the high cancer cell specificity of PNB in vivo compared to any targeted nanoparticles, since the largest clusters are self-built by aggressive cancer cells and do not emerge in normal cells (FIG. 2D). The fluence of the laser pulse was applied below the PNB generation threshold for single nanoparticles but above the PNB generation threshold for their large clusters. Thus, PNBs are selectively generated only around large clusters, that is, in cancer cells, and do not emerge in normal cells even despite unavoidable non-specific accumulation of single nanoparticles in normal cells. In addition to the high cancer cell specificity, a PNB efficiently thermally insulates the overheated gold cluster from the outer media, thus preventing any thermal bio-damage to any object outside the PNB.

Figure 11:
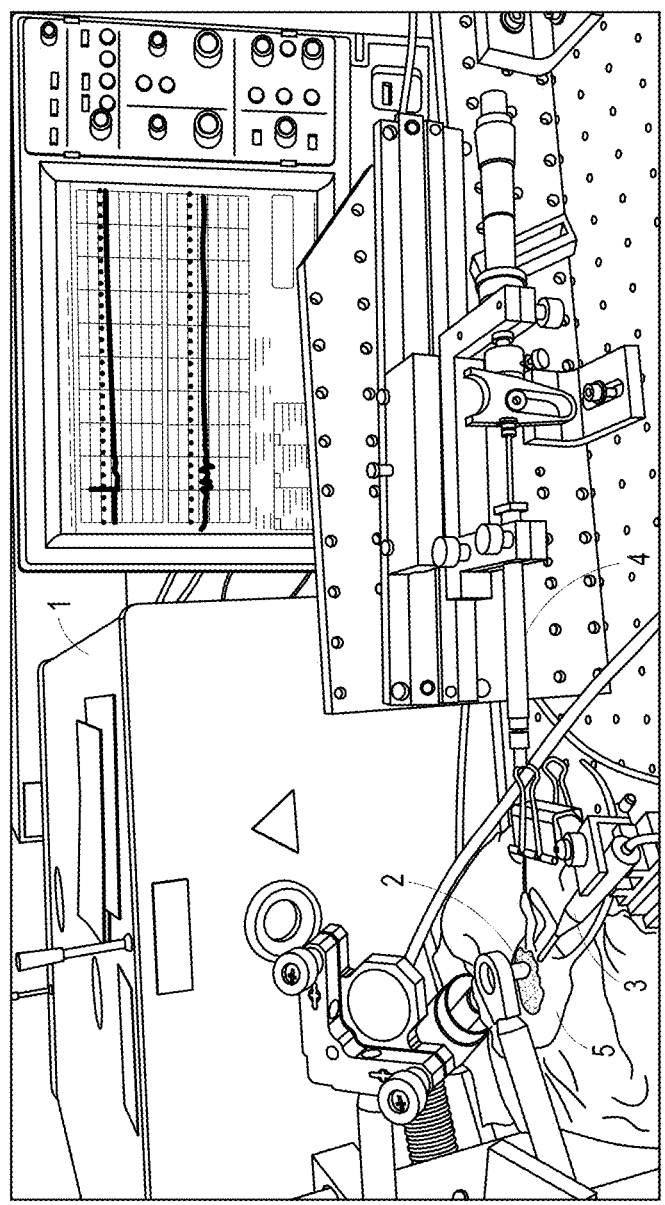
FIG. 11 illustrates an exemplary experimental setup for in vivo generation and detection of PNBs.

The laser fluence was measured through the acquisition of the beam image in the target plane (to obtain the beam diameter, we used the imagers Andor Luca EMCDD (Andor technology Ltd, Belfast, UK) and Spiricon (Ophir-Spiricon LLC, N. Logan, UT) and pulse energy meter (Ophir-Spiricon LLC, N. Logan, UT). Single cell experiments used a photothermal microscope. In the in vivo experiments, the laser pulse was delivered to the tissue via a custom endoscope in an experimental setup as shown in FIG. 11. Specifically, the exemplary experimental setup in FIG. 11 comprises (1) a pulsed NIR laser (782 nm, 30 ps); (2) an endoscope for the delivery of the laser beam (diameter 4 mm) into a surgical bed; (3) an acoustic sensor with preamplifier in the back; (4) a nanosyringe for injection of cancer cells into the surgical bed of (5) anesthetized mouse. The cells were injected into the surgical bed of a mouse in specific amounts from 3 to 100 with a 0.5 µl Hamilton nano-syringe (Sigma-Aldrich Co. LLC, St. Louis, MO) with micrometer drive (FIG. 11).

Example 5: Methods of PNB Detection

To detect PNBs optically with a single PNB sensitivity and resolution, an optical scattering method was used. A continuous probe laser beam (633 nm, 05-STP-901, Melles Griot, Rochester, NY) was focused on the PNB source and its axial intensity was monitored after the object with a high-speed photodetector (FPD 510-FV, Menlo Systems GmbH, Martinsried, Germany) connected to a digital oscilloscope (LeCroy 42xs, Teledyne LeCroy, Chestnut Ridge, NY). The vapor-liquid boundary of a PNB scatters the incident probe laser beam thus reducing its axial intensity.

The expansion and collapse of a PNB creates a specific dip-shaped pattern in the time-response of the intensity of the probe laser to a single pump laser pulse. Its duration, or lifetime, characterizes the maximal diameter of a PNB. This method directly detects individual PNBs, but only in optically transparent media.

To detect PNBs in opaque tissue (FIG. 2D), the pressure pulse emitted by the expanding and collapsing PNB was detected with a custom-built acoustic detector (Precision Acoustics Ltd, Dorset, UK) comprised of a broadband ultrasound sensor of a needle type integrated with a pre-amplifier. The sensor used an external power supply with a second pre-amplifier. The output of the second pre-amplifier was connected to a digital oscilloscope to register an acoustic time-response to a single laser pulse. In tissue, a diagnostic method based on the co-registration of the two time-responses from a cancer-free location (the reference) and from the location where cancer cells might be present (the test) was used. The differential response was determined by subtracting the reference response from the test response. For signal metrics, the peak-to-peak amplitude of the differential response was used. As a cancer diagnostic metric, a Diagnostic Index (DI), defined as the relative increase in test response amplitude ($V_{test}$) over the reference or background response amplitude ($V_{ref}$) was additionally used:

$$DI = \frac{V_{test} - V_{ref}}{V_{ref}}$$

Example 6: Detection of PNB Ex Vivo

Figure 12C:
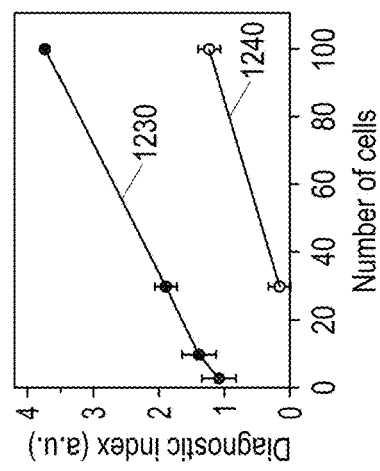
FIGS. 12A-C illustrate exemplary simultaneously detected optical scattering and acoustic time-responses to a single laser pulse applied to individual gold-pre-treated and intact HNSCC cancer cells in transparent media.
Figure 12F:
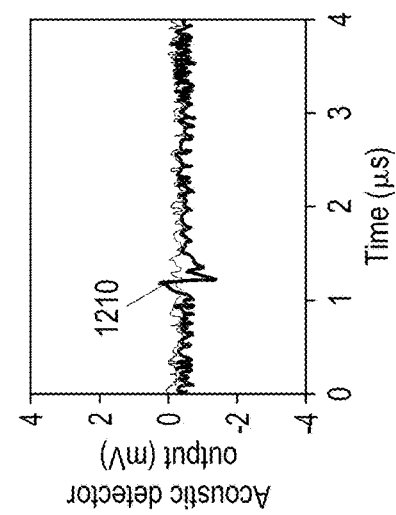
FIGS. 12D-F illustrate exemplary detected acoustic time-responses to a single laser pulse applied to individual HNSCC cancer cells in a piece of chicken breast after injecting gold pre-treated cancer cells one by one.
Figure 12B:
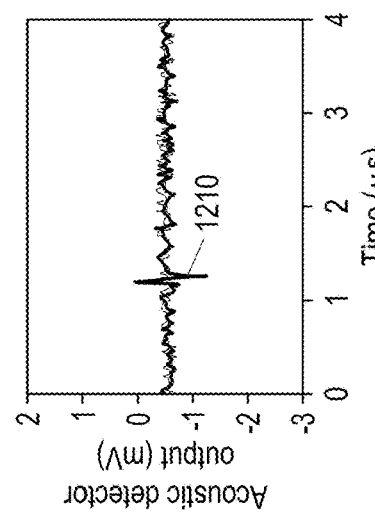
Figure 12E:
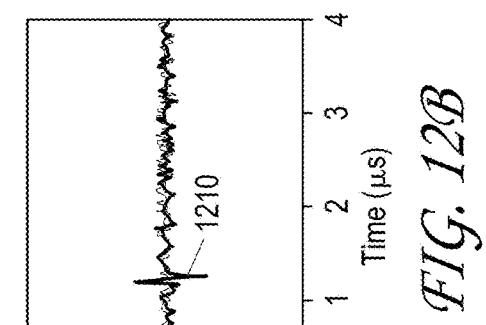
Figure 12A:
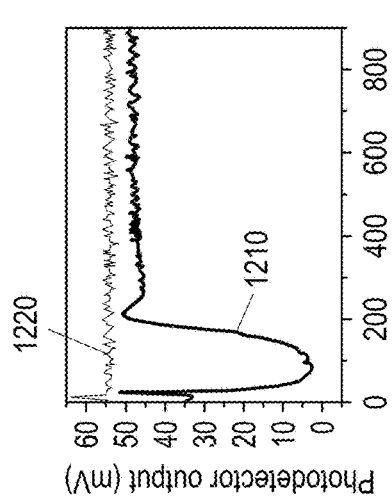

To establish a PNB diagnostic mechanism, PNBs were first generated and detected in individual gold-pretreated (60 nm spheres conjugated to Panitumumab) HNSCC cells in transparent media. PNBs were simultaneously detected optically and acoustically in response to a single laser pulse (782 nm, 30 ps) of variable fluence above the PNB generation threshold (which was found to be 10-15 mJ/cm$^2$ for gold-pretreated HNSCC cells). Above the threshold fluence, the optical signal typical for PNBs (FIG. 12A) coincided with a bipolar spike in the simultaneously detected acoustic time-response (FIG. 12B) for gold-pretreated cells 1210. No PNBs and no spikes were detected in intact (not pretreated with gold) cells 1220 under the same pulses (FIGS. 12A-12B). The amplitude of the acoustic bipolar spike almost linearly correlated to the optically measured PNB lifetime, the metric of the PNB maximal diameter (FIG. 12C). Therefore, bipolar spikes in detected acoustic time-responses were attributed to PNBs. This in vitro experiment established the principle of the acoustic detection of PNBs in single cancer cells.

Figure 12D:
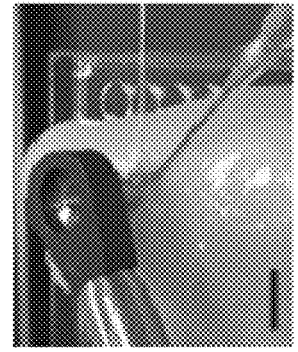
Figure 13:
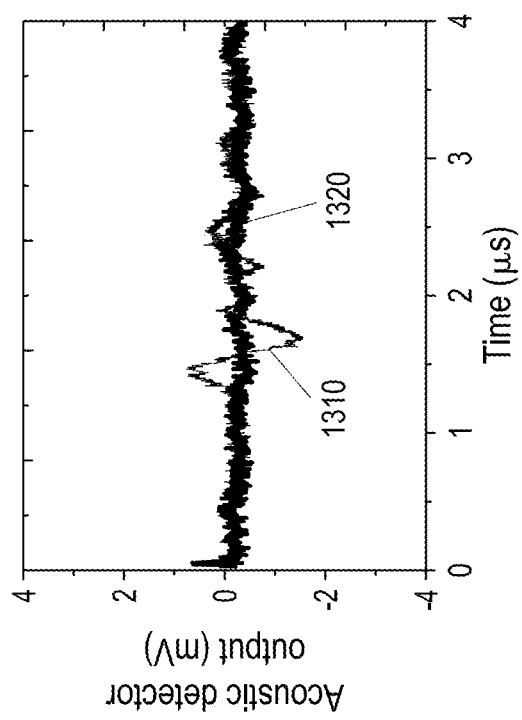
FIG. 13 illustrates exemplary acoustic time-responses to sequential laser pulses as obtained in the same location of the chicken breast in FIGS. 12D-F after injecting 10 or more gold pre-treated cancer cells.

Next, transparent cell media was replaced by a chicken breast to model intraoperative conditions of solid tissue (FIG. 12D). Gold-pretreated cancer cells were injected one by one with a nano-syringe into the tissue at a specific depth of 1 mm or 3-4 mm. A single laser pulse (782 nm, 30 ps, 70 mJ/cm$^2$, 4 mm diameter) was applied via an endoscope, and the acoustic time-response to each laser pulse was obtained with an ultrasound probe. The injection of three gold-pretreated cancer cells produced a PNB-specific spike 1210 in the acoustic time-response (FIG. 12E). No such spikes were observed after the injection of the same and a higher number of intact cells (FIG. 12E). These spikes obtained for gold-pretreated cells were similar to those obtained for PNBs in the previous experiment, and therefore were attributed to PNBs and, in this case, reported single cancer cells in solid tissue. The injection of 10 and more cells returned multiple spikes in acoustic time-responses 1310 (FIG. 13). The temporal separation of spikes in one time-response implied that the cells were spatially distributed over 2-3 mm distance in the direction of the probe axis. Thus, a single time-response reported multiple cells in different locations within the footprint of a single laser pulse. The detection procedure took about 1 ms. Next, the Diagnostic Index (the relative increase in the amplitude of the test time-response versus that of the reference, cancer-free, time-response as shown in Example 5) obtained for each cell injection was analyzed as function of the number of injected gold-pretreated cancer cells and their depths in the tissue (FIG. 12F). The Diagnostic Index was nearly proportional to the number of injected cells in the range of 3 to 100 cells. At 1 mm depth 1230, PNBs reported single cancer cells with good signal-to-background ratio. At 4 mm depth, the detection threshold increased to 30 cells 1240. These experiments established the PNB diagnostics mechanism for residual cancer cells in solid tissue at the depth comparable to that for surgical margins.

Example 7: In Vivo Intraoperative Detection of Cancer Cells

Figure 14A:
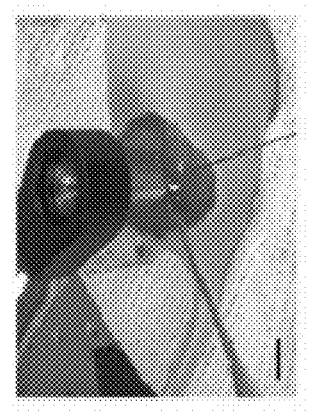
FIG. 14A illustrates an exemplary view of the mouse in FIG. 11.
Figure 14B:
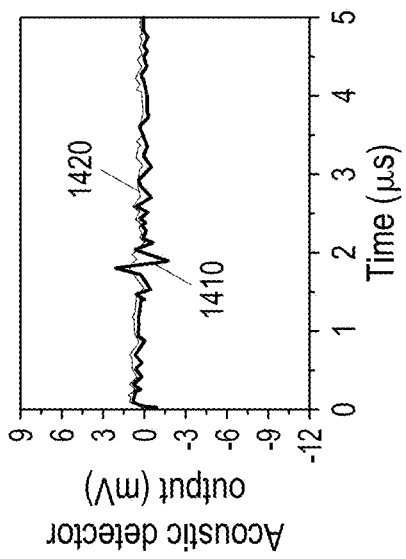
FIGS. 14B-C illustrate exemplary acoustic time-responses before and after injection of gold conjugate-pre-treated cancer cells in FIG. 14A.
Figure 14C:
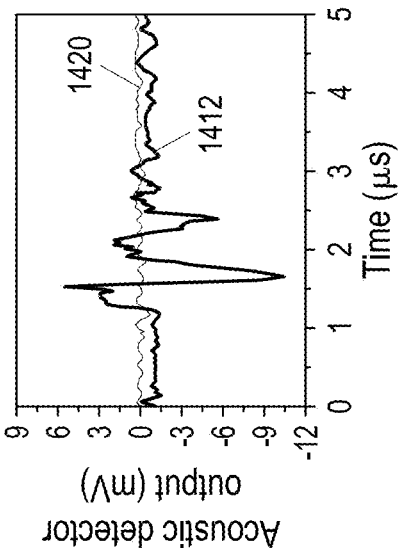
Figure 14D:
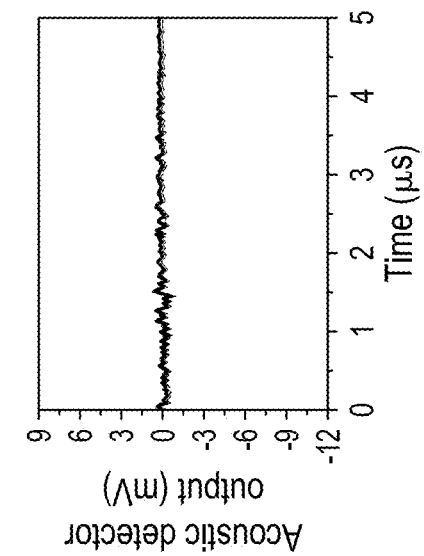
FIG. 14D illustrates exemplary acoustic time-responses before and after injection of intact (non-gold conjugate-treated) cancer cells in FIG. 14A.
Figure 14E:
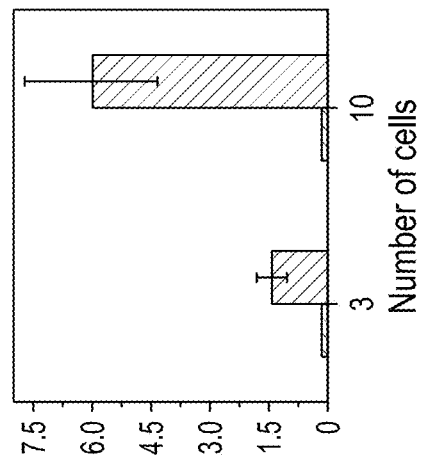
FIG. 14E illustrates an exemplary Diagnostic Index as a function of amount of injected cells for gold conjugate-pretreated and non-gold conjugate-treated cancer cells.

Individual gold-pretreated or intact cancer cells (3 and 10) were injected to the depth of 1 mm into the surgical bed of an anesthetized mouse (FIG. 14A, FIG. 11). Prior to and following each injection, a single laser pulse (782 nm, 30 ps, 70 mJ/cm$^2$, 4 mm diameter) was applied to the injection area. The acoustic time-response to the pre-injection pulse was used as a cancer-free reference signal 1420 (FIG. 14B) and the acoustic time-response to the post-injection pulse 1410 was used as a test signal. PNB-specific spikes (similar to those described above for individual gold-pretreated cancer cells) were observed after the injection of three gold-pretreated cancer cells (FIG. 14B). For ten cells, a multi-peak time-response 1412 was detected (FIG. 14C) meaning that the cells were distributed over a distance of 2-3 mm in the direction of the probe axis. Pre-injection reference signals (FIG. 14B-14D) showed minor peaks not observed in the in vitro model and could have been caused by the bulk photothermal effect in blood. This bulk effect cannot produce vapor nanobubbles (in contrast to the highly localized photothermal effect of gold clusters in cancer cells) and delivered almost identical pre- (FIG. 14D) and post-injection (FIG. 14D) signal components in time-responses of intact cells which produced no PNBs. With no false-positive signals detected for untreated cells, and no false-negative signals detected for even three gold-pretreated cells, the PNBs were highly cancer cell-specific, as can be seen from the values of the Diagnostic Index the as function of the number of cells and their gold pretreatment (FIG. 14E). In FIG. 14E, the bar on the left represents a reference, cancer-free signal and the bar on the right represents the acoustic time-response after injection of the 3 or 10 gold conjugate pre-treated cancer cells, respectively. Thus the detected PNB-positive signals were attributed to residual cancer cells in solid tissue. The time to result was within 1 ms per location of the probe. Laser pulses caused no detectable damage to the irradiated tissue in the surgical bed due to a relatively low cumulative dose (70 mJ/cm$^2$), which is well below the optical doses associated with non-invasive in vivo imaging. The safety of laser pulses and the selectivity of even large lethal PNBs can be additionally seen from the response of the cancer-normal cell mixture, identically pretreated with gold and exposed to a single broad laser pulse: even when a PNB explodes a cancer cell, surrounding normal cells survive. This high selectivity of PNBs has recently been verified for even higher laser fluences up to 140 mJ/cm$^2$.

Example 8: Probing Various Tissue Depths with Two Laser Pulses

The single pulse diagnosis processes described above are limited in solid tissues by the strong optical attenuation of the laser fluence with the tissue depth. In most of the experiments, single pulses were used at a single level of laser fluence. This is sufficient for the diagnostics of superficial MRD in surgical margins within 1-2 mm depth (which is still better than any of optical diagnosis processes whose sensitivity is limited by tens of micrometers of solid tissue depth for microscopic tumors or single cancer cells). To better accommodate the laser fluence attenuation in deeper tissues, the diagnosis process was further modified by applying two pulses in the same location, the next pulse having a higher fluence (FIG. 4A). The PNB generation threshold fluence remains the same at any tissue depth, around 10-15 mJ/cm$^2$, since the threshold at a specific laser wavelength is determined only by the size of the gold cluster. This PNB threshold, coupled with the attenuation of the laser fluence with depth, determines the maximal depth of PNB generation under a specific fluence (FIG. 4B). FIG. 4B shows the maximal tissue depth of PNB generation at the two different fluences E1 and E2>E1: the first laser pulse generates PNBs within 1 mm depth at the fluence E1, the second pulse at the fluence E2 generates PNBs within the depth range from 1 mm to 3 mm. During the second pulse, no PNBs or only small ones are generated by those cancer cells which already responded with PNBs to the first pulse because the gold cluster is usually destroyed (mechanically scattered) by the PNB (1320 in FIG. 13), and single scattered nanoparticles cannot generate PNBs under the same fluence as efficiently as clusters can. Thus, the following pulse of the higher fluence probes the deeper layer with PNBs (FIG. 4B). The laser pulse energy can be automatically switched in real time (within milliseconds) during the laser operation. In addition, the PNB generation depth is independently monitored via the time-delay from the laser pulse to the PNB spike in the time-response (FIG. 4C). This simple diagnosis process does not require signal reconstruction (unlike photoacoustic diagnosis processes) because both the PNB signal amplitude and time-delay are directly read from the primary signal. In this multi-pulse mode, PNBs not just detect deeper micro-tumors, but will also indicate the depth of the MRD, thus helping a surgeon to plan the follow-up resection.

Example 9: Intraoperative Detection and Elimination of MRD In Vivo with PNBs

The intraoperative application of PNBs depends upon the successful clustering of gold conjugates in cancer cells. In this example, systemic mechanism of in vivo gold clustering was optimized. For the combination of 60 nm gold spheres covalently conjugated to Panitumumab antibody (FIG. 10A), gold dose 4 mg/kg, time after gold injection 24 h and primary tumour size around 5 mm (FIG. 10B), both a high accumulation and specificity of gold in the tumor (FIG. 9A) were achieved. The antibody-specific "liver sink" effect, tested by comparing the gold biodistribution of anti-human and anti-mouse antibody conjugates (FIG. 9A) did not significantly influence the systemic delivery of the gold to the tumor. Although colloidal gold is clinically-safe, its short- and long-term safety in vivo (FIGS. 9B-9G) was additionally verified.

Figure 15A:
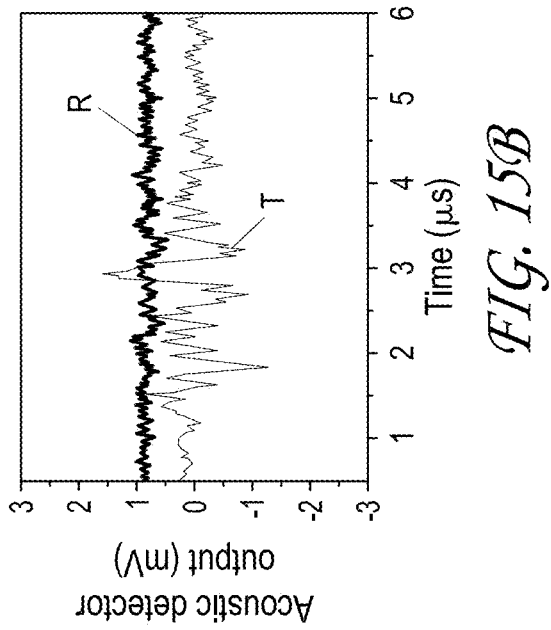
FIG. 15A illustrates an exemplary image of a surgical bed after a primary surgery.

Twenty-four hours after systemic administration of gold conjugates, PNBs were applied for the intraoperative detection and elimination of MRD in animal groups that modelled resectable and unresectable MRD. After gross resection of the primary tumor (FIG. 15A), the animals were split into three groups (1: standard surgery, 2: standard surgery +PNBs in unresectable MRD, 3: PNB-guided standard surgery in resectable MRD). After surgery, all animals were monitored for local tumor recurrence and survival.

Figure 15B:
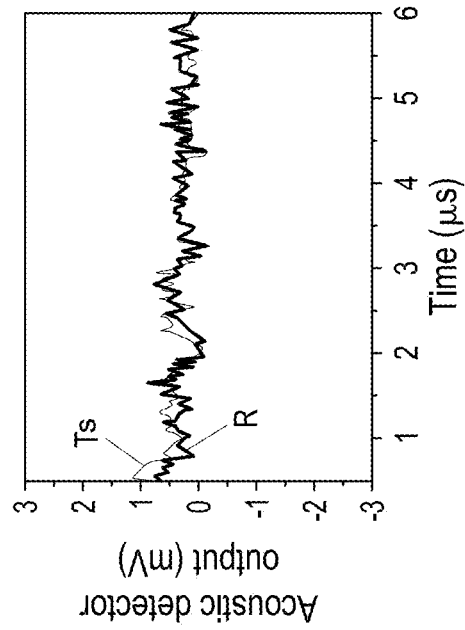
FIG. 15B illustrates exemplary acoustic time-responses to single laser pulses obtained immediately after the primary surgery in FIG. 15A at a location of possible MRD and at a MRD-negative location.
Figure 16B:
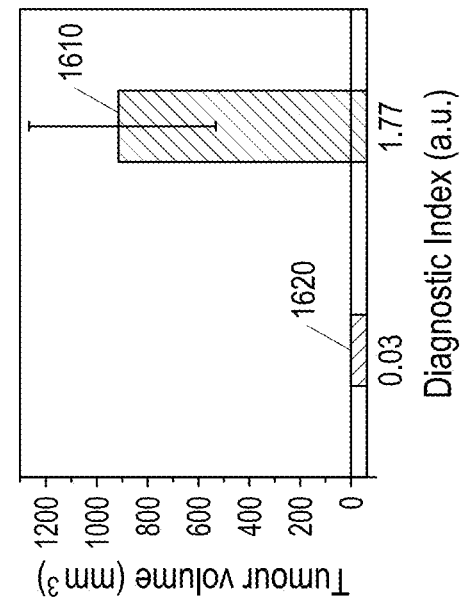
FIGS. 16A-D illustrate exemplary improvement in PNB-guided surgical outcome in both resectable and unresectable MRDs.

In Group 2 (unresectable MRD), after resecting the primary tumor, the surgical bed was scanned with PNB probe and acoustic time-responses to each pulse were collected in real time (see the surgical process shown in FIG. 6). Reference, tumor-free, signals obtained outside the tumor nest did not report PNBs (FIG. 15B, corresponds to the location marked "R" in FIG. 15A). The signals obtained inside the tumor nest reported PNB-specific spikes (FIG. 15A, corresponds to the location marked "T" in FIG. 15A) in some locations within a tumor nest in five animals (83%). These animals were intraoperatively diagnosed with PNBs as MRD-positive after primary surgery. In this group, no PNB-guided resections were applied, and thus the only treatment was the mechanical impact of PNBs. We named this mode "PNB nano-surgery". Compared to standard surgery (Group 1), PNB nano-surgery delayed local tumor recurrence (FIG. 16A) and improved animal survival by more than two-fold (FIG. 16B). The mechanical impact of PNBs destroyed cancer cells. The high cancer cell selectivity of this mechanical destruction can be clearly seen in the mixture of HNSCC and normal cells identically treated with gold conjugates and a single broad laser pulse. In response to a single laser pulse, a cancer cell literary explodes while adjacent normal cells remain unharmed. The intraoperative diagnostic PNBs did not destroy all residual cancer cells because the PNBs in some cancer cells did not reach the lethal size, while they still were able to report those cells acoustically. The surgical outcome can be further improved in this case by increasing the fluence of the laser pulse. Nevertheless, PNB nano-surgery significantly improved the surgical outcome in the most clinically challenging case of unresectable MRD.

Figure 15C:
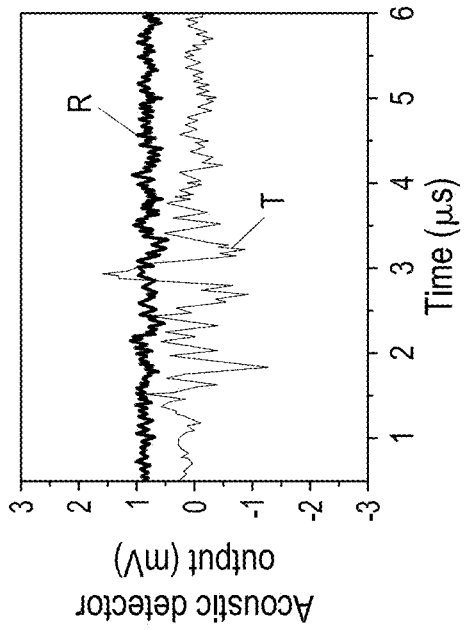
FIG. 15C illustrates an exemplary image of a surgical bed after a PNB-guided surgery.
Figure 15D:
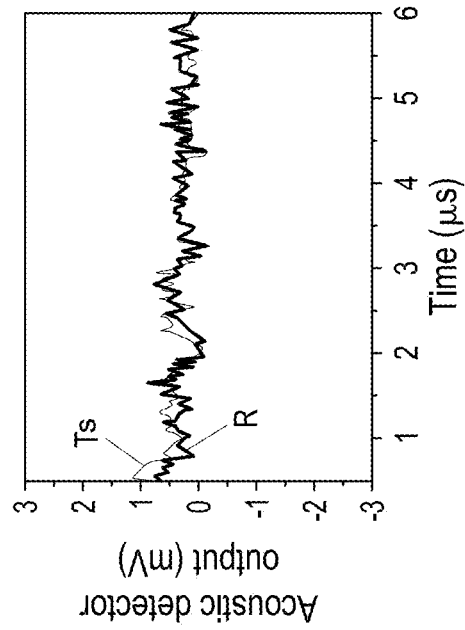
FIG. 15D illustrates exemplary acoustic time-responses obtained after the PNB-guided surgery in FIG. 15C in a location of secondary resections and in an initially MRD-negative location.

PNB-guided surgery of resectable MRD was tested in Group 3 (see the surgical process shown in FIG. 5). After the primary resection, time-responses to single laser pulses were obtained for tumor-free location ("R" in FIG. 15C) and for a tumor nest ("T" in FIG. 15C). Each PNB-positive location in the surgical bed was interpreted as MRD-positive and was subsequently further resected at 1 mm depth and 3×3 mm footprint. (FIG. 15C). After this local secondary resection, an acoustic time-response Ts was obtained again at the same location. If a PNB-positive signal was detected, additional local resection was applied again until the acoustic time-response became PNB-negative (FIG. 15D). On achieving PNB-negative time-responses in all locations (within a few minutes), wounds were closed and the animals were monitored for tumor recurrence and survival. In this group, no recurrence was observed (FIG. 16A) and complete tumor-free survival was achieved for 100% of the animals (FIG. 16B).

Figure 16D:
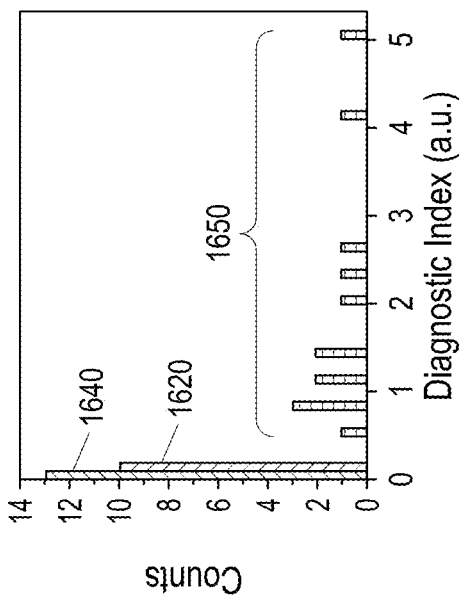
Figure 16A:
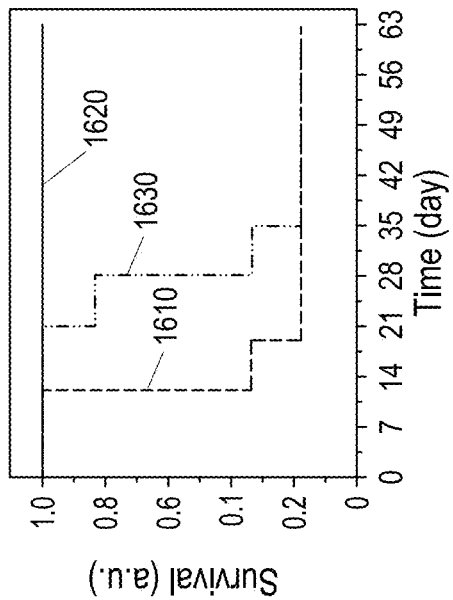
Figure 16C:
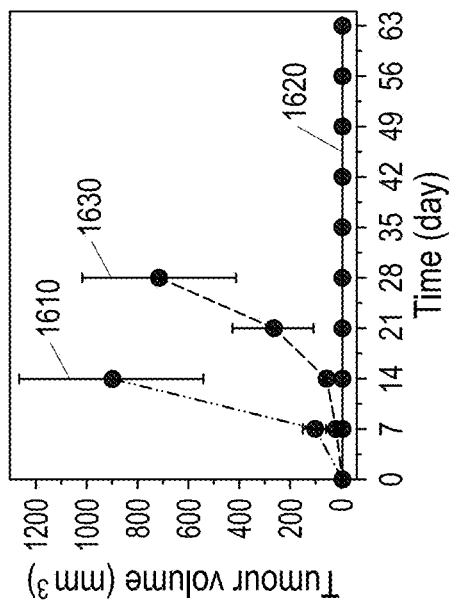

In these examples, PNBs demonstrated the unique intraoperative combination of both detecting and eliminating MRD. To determine the prognostic potential of intraoperative PNBs, we compared the Diagnostic Indexes for MRD-positive (FIG. 16C) and -negative locations (FIG. 16C) after primary surgery, and after secondary PNB-guided resections (FIG. 16C). The Diagnostic Indexes after PNB-guided resections almost coincided with those for MRD-negative tissue (FIG. 16C), thus indicating in real time the possible elimination of MRD. These intraoperatively-obtained Diagnostic Indexes were followed up by the volumes of recurrent tumors in groups treated with standard and PNB-guided surgeries (FIG. 16D). Local recurrence was associated with high Diagnostic Index (FIG. 16D). In contrast, no recurrence was associated with zero Diagnostic Index (FIG. 16D). Thus this PNB metric may serve as a prognostic index to predict the surgical outcome. As in the previous in vivo experiment, no burns or other laser- or PNB-related damage to the surgical bed in both PNB modes was observed. This experiment revealed the ability of PNBs to manage both resectable and unresectable MRDs: (1) the in vivo diagnosis of MRD with high speed and cancer specificity; (2) the prognosis of surgical outcome; (3) the improved therapeutic efficacy and reduced morbidity of standard surgery in resectable cases (which completely cured animals); and (4) the improved outcome in unresectable cases when PNBs support a "nanosurgery" mode.

Example 10: Verification of Cancer Cell Selectivity of PNBs

Unlike other thermal or mechanical events, the mechanical impact of PNB is localized within the cell where the PNB is generated and is precisely controlled with the fluence of the laser pulse. According to this data, a surface fluence of 70 mJ/cm$^2$ is safe to normal cells and even allows further increase in the fluence. In the in vitro clonogenic study of HN31 and normal cells, their identical treatment with gold and laser pulses resulted in high safety and viability of normal cells up to the laser pulse fluence levels of 140 mJ/cm$^2$ (while cancer cells were effectively destroyed with the mechanical impact of intracellular PNBs). This single cancer cell specificity of the mechanical impact of PNBs was tested in a simple experiment with the mixture of identically gold- and laser-treated normal and HNSCC cells. In this experiment, cancer and normal cells were identically pretreated in vitro with gold conjugates as described above, and 24 h later were mixed and exposed to a single broad laser pulse (which simultaneously irradiated both normal and cancer cells). Only a cancer cell explodes while adjacent normal cells remain intact and survive the laser impact and the generation of the PNB in cancer cell. This cluster-threshold PNB mechanism was verified in vivo in the primary tumor model described above. The gold cluster size was correlated with PNB metrics for tumors and normal tissues: the cluster size in vivo (directly measured with TEM in the tumor and normal adjacent tissue) was correlated to the PNB lifetime in the tissue slices harvested from a tumor and normal adjacent tissue and the amplitude of acoustic time-response. Both PNB metrics revealed the high tumor specificity of PNBs which correlated to the TEM data for gold clusters. This result was in line with the dependence of the PNB generation threshold upon the gold cluster size: the lowest around large clusters (in tumors) and the highest around single nanoparticles in adjacent normal tissue. In the current study, the gold clustering method was further verified with the results of the PNB diagnostics (FIGS. 15A-15D) and the PNB-guided surgical outcome (FIGS. 16A-16B: no PNBs would have been generated otherwise around non-clustered single gold nanoparticles). The animal group-averaged metrics of local recurrent tumors after standard surgery with resectable MRD (1610, n=6), PNB-guided surgery of resectable MRD (1620, n=5) and PNB nano-surgery of unresectable MRD (1630, n=6) show a significant improvement in the outcome in both resectable and unresectable cases when the surgery is enhanced with PNBs. FIG. 16A illustrates tumor volume versus time after the surgery. FIG. 16B illustrates animal survival rate versus time after the surgery. FIG. 16C illustrates histograms of the Diagnostic Index obtained in MRD-positive 1650 and -negative 1640 locations after standard surgery and for the MRD-positive locations 1620 after PNB-guided surgery. FIG. 16D illustrates recurrent tumor volumes plotted for the group-averaged Diagnostic Indexes after standard 1610 and PNB-guided 1620 surgery show the prognostic potential of PNBs to intraoperatively predict tumor recurrence. Thus, the gold cluster-threshold mechanism of PNB generation successfully overcomes the problem of non-specific uptake of nanoparticles by normal tissues (this problem remains the major limitation in the specificity of all material-based diagnosis processes).

Example 11: Comparison of MSOT (Multi-Spectral Optoacoustic Tomography) and PNB (Plasmonic Nanobubble) Technologies for In Vivo Intra-Operative Management of MRD (Residual Micro-Tumors) in Solid Tissues in a Surgical Bed As shown in the table below, multi-spectral optoacoustic tomography (MSOT) is not sensitive or fast enough to detect MRD (which can be represented by tens of cancer cells) in vivo in solid tissue in real time, and did not show a good surgical outcome in MRD applications when compared to the PNB technology for in vivo intraoperative management of MRD.

| Parameter/property | MSOT (as report in NPL references) | PNB |
|---|---|---|
| Intraoperative MRD detection in vivo (in surgical bed) in solid tissue | Not reported | Yes, compatible with standard surgery |
| Influence on the surgical outcome (local recurrence and overall survival) | Not reported | Yes, multi-fold improvement in survival in resectable and unresectable cases |
| Tumour detection sensitivity in solid tissue in vivo | >1 mm, >2500 cells (mouse macrophages) | Single cells and microtumours of size << 1 mm (undetectable with standard pathology) |
| Time to result in vivo for solid tissue | 150 μs - 20 min, not reported for MRD | <10 μs per location (detection), less than 1 min per 2 × 2 cm surgical bed (including the surgery involved) |

| Parameter/property | MSOT (as report in NPL references) | PNB |
|---|---|---|
| Requirements for diagnostic agents | Several different dyes or nanoparticles | Single type clinically-validated agent - colloidal gold |
| Requirements for laser radiation | Several laser beams with different wavelengths, multiple pulses | Single laser beam, single pulse, single wavelength |
| Complexity of signal interpretation | High: Reconstruction and processing of primary signals required | Low: Direct measurement of the amplitude of primary signal |

Example 12: Elimination of TMD

Figure 18:
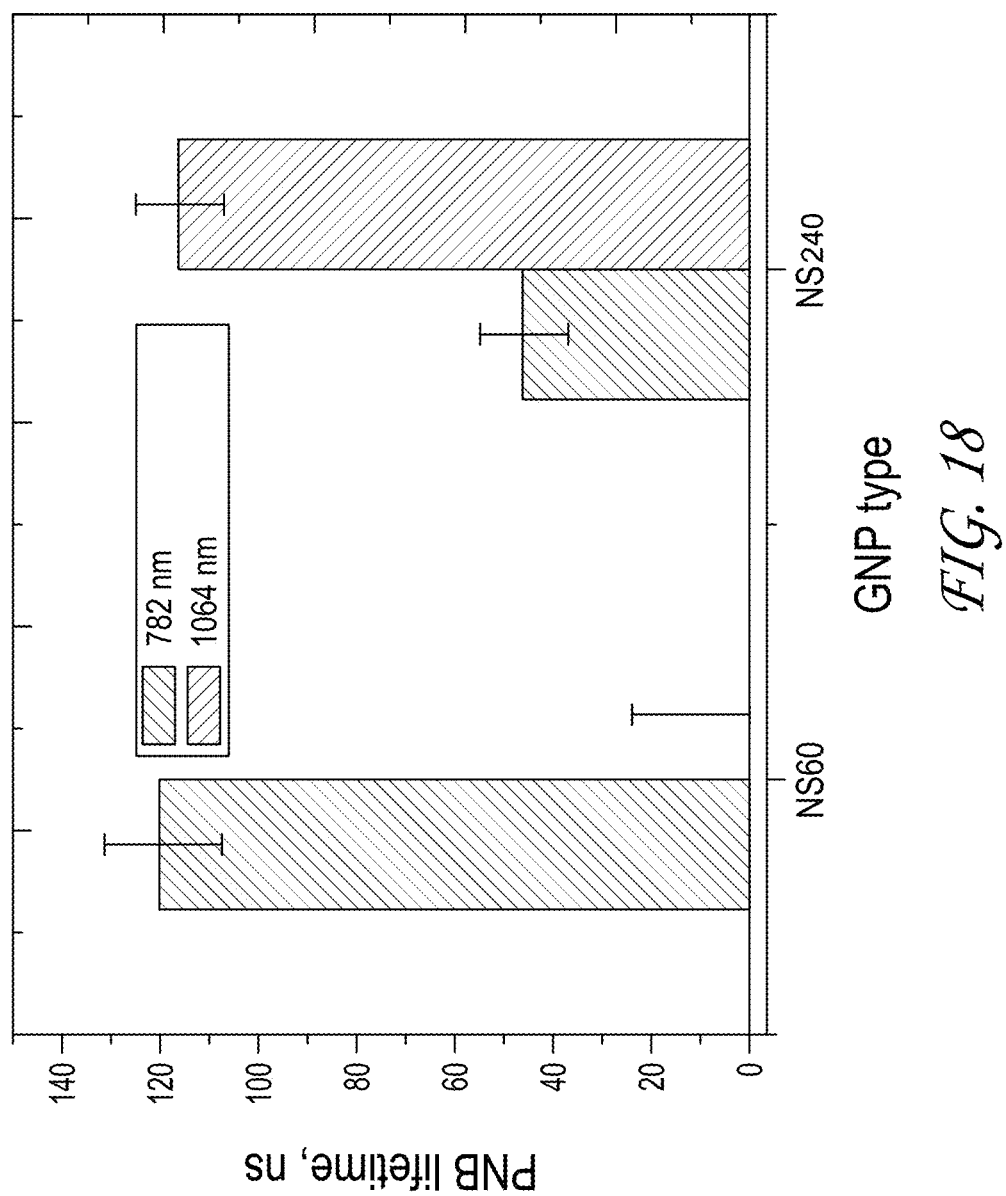
FIG. 18 illustrates exemplary PNB lifetimes of nanoparticles of different sizes and under different laser pulse energy levels.

New clinically-relevant gold spheres (240 nm) were tested in HNSCC cancer cells for the generation of PNBs on the epithelial wall of the tumor-specific vasculature under excitation with a 1064 nm laser pulse. Compared to the 782 nm pulses/60 nm nanoparticles, the tissue penetration depth can be improved 2-3 fold, and technical complexity of the laser reduced by half without increasing the cost of the laser system. New nanoparticle/laser wavelength combination showed the efficacy similar to that for the combination of 782 nm laser pulses/60 nm nanoparticles, as illustrated by the lifetime of PNBs generated in cancer cells treated with standard and new combination in FIG. 18. Laser pulses at 1064 nm are more available, less expensive and can deliver 10× fold energy compared to 782 nm laser pulses. This is the new option that requires specific nanoparticles with high PNB generation efficacy at 1064 nm. It is possible that higher energy at lower cost (10% of that for current 782 nm) will support deeper tissue penetration at 1064 nm and hence will improve the therapeutic efficacy of the mono PNB therapy.

Additional embodiments of the present disclosure, such as system and process for intraoperatively detecting and precisely eliminate TME including but not limited to tumor blood vasculature are provided in Appendices A and B. In one embodiment, vasculature-specific bioconjugated nanoparticles are administered to tissue. The bioconjugated nanoparticles comprise nanoparticles conjugated with vascular-specific ligands. After a predetermined time delay, such as 24 hours, laser pulses with a wavelength or fluence sufficient for creating vasculature-specific PNBs are applied to the tissue to cause destruction of tumor-vasculature.

Although the foregoing has been described in terms of certain specific embodiments, other embodiments will be apparent to those of ordinary skill in the art from the disclosure herein. Moreover, the described embodiments have been presented by way of example only, and are not intended to limit the scope of the disclosure. Indeed, the novel methods and systems described herein may be embodied in a variety of other forms without departing from the spirit thereof. Accordingly, other combinations, omissions, substitutions, and modifications will be apparent to the skilled artisan in view of the disclosure herein. Thus, the present disclosure is not limited by the disclosed embodiments, but is defined by reference to the appended claims. The accompanying claims and their equivalents are intended to cover forms or modifications as would fall within the scope and spirit of the disclosure.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

What is claimed is:

1. A system configured to be used in resection of cancer cells or microtumors, said system comprising:
   a plasmonic nanobubbles ("PNB") probe configured to be coupled to a source of electromagnetic radiation to irradiate a first location of a tissue of a patient that includes bioconjugated nanoparticles at a first energy level to produce PNBs in said tissue, wherein the source is further configured to, when needed, provide the PNB probe with increasing levels of radiation pulses than the first energy level to reach increasing depths of the tissue;
   a detector configured to output a response signal responsive to pressure pulses emitted by said PNBs from at least some of the bioconjugated nanoparticles when said tissue includes said cancer cells or microtumors; and
   a control system including a signal processor operably communicating with said detector and configured to process information responsive to said response signal to generate an output to a clinician,
   wherein, in response to the output indicating presence of a PNB, the control system is configured to instruct resection of a portion of said tissue at the first location defined by a footprint of the PNB probe, and
   in response to the output indicating absence of a PNB, the control system is further configured to compare a time response of the response signal with a threshold and output a final instruction based on said comparison.

2. The system of claim 1, further comprising a robotic surgical arm configured to position or house said PNB probe.

3. The system of Claim 1, wherein the final instruction is to resect more of said portion even when said processing the information does not indicate a presence of said PNBs.

4. The system of Claim 1, wherein the final instruction further includes directing a clinician to probe deeper into said portion of said tissue by irradiating the tissue at the first location at a higher energy level than the first energy level.

5. The system of claim 1, wherein, in response to the output indicating presence of a PNB, the control system is further configured to instruct irradiation of the first location at the first energy level after the resection.

6. The system of claim 1, further comprising a laparoscopic tool or an endoscope configured to position or house said PNB probe.

7. The system of claim 1, wherein the final instruction further includes directing a clinician to relocate said PNB probe to a different portion of said tissue.

8. A process that guides a surgeon in resection of cancer cells or microtumors, said process comprising:
   irradiating, with a plasmonic nanobubbles ("PNB") probe having a source of electromagnetic radiation, a first location of a tissue of a patient that includes bioconjugated nanoparticles at a first energy level to produce PNBs in said tissue, wherein the source is further configured to, when needed, provide the PNB probe with increasing levels of radiation pulses than the first energy level to reach increasing depths of the tissue;
   outputting from a detector a response signal responsive to pressure pulses emitted by said PNBs from at least some of the bioconjugated nanoparticles when said tissue includes said cancer cells or microtumors;
   processing with a digital signal processor information responsive to said response signal to generate an output to a clinician; and
   in response to the output indicating presence of a PNB, instructing resection of a portion of said tissue at the first location defined by a footprint of the PNB probe, and
   in response to the output indicating absence of a PNB, comparing a time response of the response signal with a threshold and outputting a final instruction based on the comparison.

9. The process of claim 8, wherein said irradiating, outputting, processing, and generating repeats with each resection of said portion of said tissue.

10. The process of claim 8, wherein the final instruction is to resect more of said portion even when said processing does not indicate a presence of said PNBs.

11. The process of claim 8, wherein the final instruction further includes directing said surgeon to probe deeper into said portion of said tissue by irradiating the tissue at the first location at a higher energy level than the first energy level.

12. The process of claim 11, wherein said irradiating at the higher energy level comprises pulsing said source at a laser pulse fluence of between 10 mJ/cm$^2$ and 120 mJ/cm$^2$.

13. The process of claim 12, wherein said pulsing said source at said laser pulse fluence comprises pulsing said source at about 60 mJ/cm$^2$.

14. The process of claim 8, wherein said irradiating comprises pulsing said source for a duration not exceeding about 100 ps.

15. The process of claim 8, wherein said irradiating comprises pulsing said source for a duration of about 30 ps.

16. The process of claim 8, further comprising, in response to the output indicating presence of a PNB, using the PNB probe to iteratively irradiate the first location of the tissue at the first energy level until the output indicates absence of a PNB.

17. The process of claim 8, wherein instructing resection of the portion of said tissue at the first location defined by the footprint of the PNB probe comprises sending a command to a robotic surgical arm to perform the resection.

18. The process of claim 8, wherein the final instruction further includes directing a clinician to relocate said PNB probe to a different portion of said tissue.

* * * * *